US006100254A

United States Patent [19]
Budde et al.

[11] Patent Number: 6,100,254
[45] Date of Patent: Aug. 8, 2000

[54] INHIBITORS OF PROTEIN TYROSINE KINASES

[75] Inventors: Raymond J. A. Budde, Bellaire, Tex.; Jonathan A. Ellman, Oakland, Calif.; Victor A. Levin, Houston, Tex.; Gary E. Gallick, Kingwood, Tex.; Robert A. Newman, Sugar Land, Tex.

[73] Assignees: Board of Regents, The University of Texas System, Austin, Tex.; The Regents of the University of California, Oakland, Calif.

[21] Appl. No.: 08/948,839

[22] Filed: Oct. 10, 1997

[51] Int. Cl.$^7$ .................. A61K 31/5513; A61P 25/00; C07D 243/16

[52] U.S. Cl. .................. 514/221; 540/504; 540/506; 540/507; 540/508; 540/509; 540/510; 540/511; 540/512; 540/513; 540/514

[58] Field of Search .................. 514/221; 540/504, 540/506, 507, 508, 509, 510, 511, 512, 513, 514

[56] References Cited

U.S. PATENT DOCUMENTS

| | | | |
|---|---|---|---|
| 5,288,514 | 2/1994 | Ellman | 427/2 |
| 5,532,359 | 7/1996 | Martstes, Jr. et al. | 540/522 |
| 5,545,568 | 8/1996 | Ellman | 436/518 |
| 5,569,654 | 10/1996 | Armour et al. | 514/221 |
| 5,618,812 | 4/1997 | Castro Pineiro et al. | 514/221 |
| 5,631,251 | 5/1997 | Butcher et al. | 514/221 |
| 5,633,251 | 5/1997 | Claremon et al. | 514/221 |
| 5,688,943 | 11/1997 | Ryder et al. | 540/509 |

FOREIGN PATENT DOCUMENTS

WO93/00095 of 1993 WIPO.

OTHER PUBLICATIONS

Jessup and Gallick; "The Biology of Colorectal Carcinoma," *Curr. Probl. Cancer*, 16:265, 1992.

Choong and Ellman, "Solid–Phase Synthesis: Applications to Combinatorial Libraries," in *Annual Reports in Medicinal Chemistry*; Trainor, Ed.; Academic Press, Inc., 1996, pp. 309–318.

Aggarwal, Totpal, Ali–Osman, Budde, Pocsik, "pp60$^{v-src}$ Kinase Overexpression Leads to Resistance to the Antiproliferative Effects of Tumor Necrosis Factor" *FEBS Lett.*, 345:219, 1994.

Barnekow, "Functional Aspects of the c–src Gene," *Crit. Rev. Oncogenesis*, 1:277, 1989.

Becker, Meier, Herlyn, "Proliferation of Human Malignant Melanomas is Inhibited by Antisense Oligodeoxynucleotides Targeted Against Basic Fibroblast Growth Factor," *The EMBO Journal*, 8(12):3685, 1989.

Bjelfman, Hedborg, Johansson, Nordenskjold, Pahlman, "Expression of the Neuronal Form of pp60$^{c-src}$ in Neuroblastoma in Relation to Clinical Stage and Prognosis," *Cancer Res.*, 50:6908, 1990.

Bock, Dipardo, Evans, Rittle, Whitter, Veber, Anderson, Freidinger, "Benzodiazepine Gastrin and Brain Cholecystokinin Receptor Ligands: L–365,260" *J. Med. Chem.*, 32:13, 1989.

Bolen, Rosen, Israel, "Increased pp60$^{c-src}$ Tyrosyl Kinase Activity in Human Neuroblastomas is Associated With Amino–Terminal Tyrosine Phosphorylation of the src Gene Product," *Proc. Natl. Acad. Sci.*, 82:7275, 1985.

Bolen, Veillette, Schwartz, Deseau, Rosen, "Activation of pp60$^{c-src}$ Protein Kinase Activity in Human Colon Carcinoma," *Proc. Natl. Acad. Sci. USA*, 84:2251, 1987.

Bolen, Veillette, Schwartz, Deseau, Rosen, "Analysis of pp60$^{c-src}$ in Human Colon Carcinoma and Normal Human Colon Mucosal Cells," *Oncogene Res.*, 1:149, 1987.

Boojamra, Burow, Ellman, "A General and Straightforward Method for the Solid–Phase Synthesis of 1,4–Benzodiazepine–2,5–diones" *J. Org. Chem.* 60:5742, 1995.

Boojamra, Burow, Thompson, Ellman "Solid–Phase Synthesis of 1,4–Benzodiazepine–2,5–diones. Library Preparation and Demonstration of Synthesis Generality" *J. Org. Chem.* 62:1240, 1997.

Budde, Ke, Levin, "Activity of pp60$^{c-src}$ in 60 Different Cell Lines Derived from Human Tumors," *Cancer Biochem. Biophys.*, 14:171, 1994.

Budde, Obeyesekere, Ke, McMurray, "Use of Synthetic Peptides and Copolymers to Study Substrate Specificity and Inhibition of the Protein Tyrosine Kinase pp60$^{c-src}$," *Biochem. Biophys. Acta.*, 1248:50, 1995.

Budde, "Evidence for Kinetically Distinct Forms of pp60$^{c-src}$ with Different $K_m$ Values for their Protein Substrate" *J. Biol. Chem.* 268:24868, 1993.

Budde, McMurray, Saya, Gallick, Levin "Discovery, Development and Testing of Substrates and Inhibitors of pp60$^{c-src}$" *Int. J. Pharmacog.*, 33:27, 1995.

Bunin and Ellman, "A General and Expedient Method for the Solid–Phase Synthesis of 1,4–Benzodiazepine Derivatives" *J. Am. Chem. Soc.* 114:10997, 1992.

Bunin and Ellman, "Increasing the Diversity of a 1,4–Benzodiazepine Library through Side–Chain Functionalization" *Polymer Preprints*, 35:983, 1994.

Bunin, Plunkett, Bray, Ellman, "The Synthesis of a 1680 Compound 1,4–Benzodiazepine Library" *New J. Chem.* 21:125, 1997.

Bunin, Plunkett, Ellman "Synthesis and Evaluation of 1,4–Benzodiazepine Libraries" *Methods Enzymol.*, 267:448, 1996.

(List continued on next page.)

*Primary Examiner*—Richard L. Raymond
*Assistant Examiner*—Brenda Coleman
*Attorney, Agent, or Firm*—Fulbright & Jaworski

[57] ABSTRACT

Disclosed herein are small molecule, non-peptidyl inhibitors of protein tyrosine kinases, and methods for their use. The instant inhibitors are based on a 1,4-benzodiazepin-2-one nucleus. Methods are provided for inhibition of specific protein tyrosine kinases, for example pp60$^{c-src}$. Methods are further provided for the use of these inhibitors in situations where the inhibition of a protein tyrosine kinase is indicated, for example, in the treatment of certain diseases in mammals, including humans.

31 Claims, 7 Drawing Sheets

OTHER PUBLICATIONS

Bunin, Plunkett, Ellman "The Combinatorial Synthesis, and Chemical and Biological Evaluation of a 1,4–Benzodiazepine Library" *Proc. Natl. Acad. Sci USA*, 91:4708, 1994.

Burke, Jr. "Protein–Tyrosine Kinase Inhibitors," *Drugs of the Future*, 17:119, 1992.

Burke, Jr. "Protein–Tyrosine Kinases: Potential Targets for Anticancer Drug Design," *Stem Cells*, 12:1, 1994.

Burke, Jr., Lim, Marquez, Li, Bolen, Stefanova, Horak, "Bicyclic Compounds as Ring Constrained Inhibitors of Protein–Tyrosine Kinase $p56^{lck}$," *J. Med. Chem.*, 36:425, 1993.

Cartwright, Kamps, Meisler, Pipas, Eckhart, "$pp60^{c-src}$ Activation in Human Colon Carcinoma," *J. Clin. Invest.*, 83:2025, 1989.

Cartwright, Meisler, Eckhart, "Activation of the $pp60^{c-src}$ Protein Kinase is an Early Event in Colonic Carcinogenesis," *Proc. Natl. Acad. Sci. USA*, 87:558, 1990.

Chackalaparampil and Shalloway, "Altered Phosphorylation and Activation of $pp60^{c-src}$ During Fibroblast Mitosis" *Cell*, 52:801, 1988.

Chang and Geahlen, "Protein–Tyrosine Kinase Inhibition: Mechanism–Based Discovery of Anti–Tumor Agents," *J. Nat. Prod.*, 55:1529, 1992.

Chen, Boiziau, Parker, Maillet, Commercon, Tocque, LePecq, Roques, Garbay, "Structure–Activity Relationships in a Series of 5–[(2,5–dihydroxybenzyl)amino] Salicylate Inhibitors of EGF–Receptor–Associated Tyrosine Kinase: Importance of Additional Hydrophobic Aromatic Interactions," *J. Med. Chem.*, 37:845, 1994.

Coyle and Puttfarcken, "Oxidative Stress, Glutamate, and Neurodegenerative Disorders," *Science* 262:689, 1993.

Cushman, Chinnasamy, Chakkraborti, Jurayj, Geahlen, Haugwitz, "Synthesis of [(4–pyridyl–1–oxide)–L-Alanine$^4$]–Angiotensin I as a Potential Suicide Substrate for Protein– Tyrosine Kinases," *Int. J. Pept. Prot. Res.*, 36:538, 1990.

Cushman, Nagarathnam, Burg, Geahlen, "Synthesis and Protein–Tyrosine Kinase Inhibitory Activities of Flavonoid Analogues," *J. Med. Chem.*, 34:798, 1991.

Cushman, Nagarathnam, Gopol, Geahlen, "Synthesis and Evaluation of New Protein–Tyrosine Kinase Inhibitors. Part 1. Pyridine–Containing Stilbenes and Amides," *Biorg. Med. Chem. Lett.*, 1:211, 1991.

Cushman, Nagarathnam, Gopal, Geahlen, "Synthesis and Evaluation of New Protein–Tyrosine Kinase Inhibitors. Part 2. Phenylhydrazones," *Biorg. Med. Chem. Lett.*, 1:215, 1991.

Dow, Chou, Bechle, Goddard, C. and Larson, E.R. "Identification of Tricyclic Analogs Related to Ellagic Acid as Potent/Selective Tyrosine Protein Kinase Inhibitors," *J. Med. Chem.*, 37:2224, 1994.

Ellman, "Combinatorial Organic Libraries" *Chemtracts: Org. Chem.*, 8(1):1, 1995.

Ellman, "Design, Synthesis, and Evaluation of Small–Molecule Libraries" *Acc. Chem. Res.*, 29: 132, 1996.

Ellman, "Synthesis and Evaluation of Three 1,4–Benzodiazepine Libraries" in *Combinatorial Peptide and Nonpeptide Libraries*; Jung, G., Ed.; VCH Verlagsgesellschaft mbH: Weinham, Germany, 1996, pp. 405–424.

Ellman, "The Solid–Phase Synthesis of Complex Small Molecules" *Chimia* 50:260, 1996.

Ellman, Stoddard, Wells, "Combinatorial Thinking in Chemistry and Biology" *Proc. Natl. Acad. Sci., USA* 94:2779, 1997.

Fanning, Bulovas, Saini, Libertino, Joyce, Summerhayes, "Elevated Expression of $pp60^{c-src}$ in Low Grade Human Bladder Carcinimoa," *Cancer Res*, 52:1457, 1992.

Fry, Kraker, McMichael, Ambroso, Nelson, Leopold, Conners, Bridges, "A Specific Inhibitor of the Epidermal Growth Factor Receptor Tyrosine Kinase," *Science*, 265:1093, 1994.

Garcia, Parikh, Saya, Gallick, "Effect of Herbimycin A on Growth and $pp60^{c-src}$ Activity in Human Colon Tumor Cell Lines," *Oncogene*, 6:1983, 1991.

Hall, Schaeublin, Missbach, "Evidence that c–src is Involved in the Process of Osteoclastic Bone Resorption," *Biochem. Biophys. Res. Commun.*, 199:1237, 1994.

Heresco–Levy, Silipo, Javitt "Glycerinergic Augmentation of NMDA Receptor–Mediated Neurotransmission in the Treatment of Schizophrenia," *Psychopharm. Bull.* 32(4):731, 1996.

Honeggar, Dull, Szapary, Komoriya, Kris, Ullrich, Schlessinger, "Kinetic Parameters of the Protein Tyrosine Kinase Activity of EGF–Receptor Mutants with Individually Altered Autophosphorylation Sites," *EMBO J.*, 7:3053, 1988.

James, Goldstein, Brown, Rawson, Somers, McDowell, Crowley, Lucas, Levinson, Marsters, "Benzodiazepine Peptidomimetics: Potent Inhibitors of Ras Farnesylation in Animal Cells,"*Science*, 260:1937, 1993.

Kitanaka, Waki, Kamano, Tanaka, "Antisense src expression Inhibits Proliferation and Erythropoietin–Induced Erythroid Differentiation of K562 Human Leukemia Cells," *Biochem. Biophysic Res. Commun.*, 201:1534, 1994.

Kornecki, Ehrlich, Lenox, "Platelet–Activating Factor–Induced Aggregation of Human Platelets Specifically Inhibited by Triazolobenzodiazepines" *Science*, 226:1454, 1984.

Li, Ke, Budde, "The C–Terminal Src Kinase (CSK) is Widely Expressed, Active in HT–29 Cells That Contain Activated Src, and its Expression is Downregulated in Butyrate–Treated SW620 Cells" *Cell Biol. Int.* 20:723, 1996.

Luttrell, Lee, Lansing, Crosby, Jung, Willard, Luther, Rodriguez, Berman, Gilmer, "Involvement of $pp60^{c-src}$ with Two Major Signaling Pathways in Human Breast Cancer," *Proc. Natl. Acad. Sci.*, 91:83, 1994.

Lynch, Brugge, Fromowitz, Glantz, Wang, Caruso, Viola, "Increased Expression of the src Proto–Oncogene in Hairy Cell Leukemia and a Subgroup of B–Cell Lymphomas," *Leukemia*, 7:1416, 1993.

Maguire, Sheets, McVety, Spada, Zilberstein, "A New Series of PDGF Receptor Tyrosine Kinase Inhibitors: 3–Substituted Quinoline Derivatives," *J. Med. Chem.*, 37:2129, 1994.

McMurray, Budde, Dyckes, "Cyclic Peptide Substrates of pp60c–src: Synthesis and Evaluation" *Int. J. Peptide & Protein Res.* 42:209, 1993.

Navarro, Ghany, Racker, "Inhibition of Tyrosine Protein Kinases by Halomethyl Ketones," *Biochemistry*, 21:6138, 1982.

Nishi, Budde, McMurray, Obeyesekere, Safdar, Saya, "Construction and Use of a Random 15–Amino Acid Peptide Library to Identify Tight–Binding Inhibitory Sequences Against $pp60^{c-src}$," *FEBS Lett.* 399:237, 1996.

Novotny–Smith and Gallick, "Growth Inhibition of Human Colorectal Carcinoma Cell Lines by Tumor Necrosis Factor Alpha Correlates with Reduced Activity in $pp60^{c-src}$", *J. Immunother*, 11:159, 1992.

O'Shaughnessy, Deseau, Amini, Rosen, Bolen, "Analysis of the c–src Gene Product Structure, Abundance, and Protein Kinase Activity in Human Neuroblastoma and Glioblastoma Cells," *Oncogene Res.*, 2:1, 1987.

Obeyesekere, LaCroix, Budde, Dyckes, McMurray, "Solid Phase Synthesis of (Tyrosyl–Alanyl–Glutamyl)$_n$ by Segment Condensation" *Int. J. Peptide & Protein Res.* 43:118, 1994.

Ottenhoff–Kalff, Rijksen, van Beurden, Hennipman, Michels, Staal, "Characterization of Protein Tyrosine Kinases From Human Breast Cancer: Involvement of the c–src Oncogene Product," *Cancer Res.*, 52:4773, 1992.

Partanen, "Immunohistochemically Demonstrated pp60$^{c-src}$ in Human Breast Carcinoma," *Oncology Reports* 1:603, 1994.

Plunkett and Ellman, "A Silicon–Based Linker for Traceless Solid–Phase Synthesis," *J. Org. Chem.*, 60:6006, 1995.

Plunkett and Ellman, "Combinatorial Chemistry and New Drugs" *Sci. Am.* 276:68, 1997.

Plunkett and Ellman, "Solid Phase Synthesis of Structurally Diverse 1,4–Benzodiazepine Derivatives Using the Stille Coupling Reaction" *J. Am. Chem. Soc.*, 117:3306, 1995.

Preis, Saya, Nadasdi, Hochhaus, Levin, Sadee, "Neuronal Cell Differentiation of Human Neuroblastoma Cells by Retinoic Acid Plus Herbimycin–A," *Cancer Res.*, 48:6530, 1988.

Punt, Rijksen, Vlug, Dekker, Staal, "Tyrosine Protein Kinase Activity in Normal and Leukemic Human Blood Cells," *Brit. J. Hematology*, 73:51, 1989.

Ramdas and Budde, "The Instability of Polyhydroxylated Aromatic Protein Tyrosine Kinase Inhibitors in the Presence of Manganese," *Cancer Biochem. Biophys.* (in press, 1997).

Ramdas, McMurray, Budde, "The Degree of Inhibition of Protein Tyrosine Kinase Activity by Tyrphostin 23 and 25 is Related to their Instability" *Cancer Research* 54:867, 1994.

Ramdas, Obeyesekere, McMurray, Gallick, Seifert, Budde, "A Tyrphostin–Derived Inhibitor of Protein Tyrosine Kinases: Isolation and Characterization," *Archiv. Biochem. Biophys.* 323:237, 1995.

Ramdas, Obeyesekere, McMurray, Budde, "A Synthetic Peptide Substrate of Minimal Size and Semi–Optimal Sequence for the Protein Tyrosine Kinase pp60$^{c-src}$," *Archiv. Biochm. Biophys.* 326:73, 1996.

Romer, Buscher, Hill, Maurer, Petcher, Zeugner, Benson, Finner, Milkowski, Thies, "An Opioid Benzodiazepine," *Nature*, 298:759, 1982.

Rosen, Bolen, Schwartz, Cohen, Deseau, Israel, "Analysis of pp60$^{c-src}$ Activity in Human Tumor Cell Lines and Tissues," *J. Biol. Chem.*, 261:13754, 1986.

Sabe, Okada, Nakagawa, Hanafusa, "Activation of c–Src in Cells Bearing v–Crk and Its suppression by Csk," *Mol Cell Biol.*, 12:4706–4713, 1992.

Shoelson, White, Kahn, "Nonphosphorylatable Substrate Analogs Selectively Block Autophosphorylation and Activation of the Insulin Receptor, Epidermal Growth Factor, and pp60$^{v-src}$ Kinases," *J. Biol. Chem.*, 264:7831, 1989.

Soriano, Montogomery, Geske, Bradley, "Targeted Disruption of the c–src Proto–Oncogene Leads to Osteopetrosis in Mice," *Cell*, 64:693, 1991.

Staley, Parikh, Saya, Gallick, "Inhibition of in vitro and in vivo HT–29 Colon Adenocarcinoma Cell Line Growth by a c–src Antisense Expression Vector," oral presentation, AACR Annual Meeting, Toronto, Canada, 1995.

Sternbach, "The Benzodiazepine Story" *J. Med. Chem.*, 22:1, 1979.

Sun and Budde, "Expression, Purification and Initial Characterization of Human Yes Protein Tyrosine Kinase from a Bacterial Expression System," *Archiv. Biochem. Biophys.*, 345:135, 1997.

Sun and Budde "Requirement for an Additional Divalent Metal Cation to Activate Protein Tyrosine Kinases," *Biochemistry* 36:2139, 1997.

Sun, Ke, Budde, "Csk Phosphorylation and Inactivation In Vitro by the cAMP–Dependent Protein Kinase," *Archiv. Biochem. Biophys.* 343:194, 1997.

Takeshima, Hamaguchi, Watanbe, Aldyama, Kataoka, Ohnishi, Xiao, Nagai, Takagi, "Aberrant Elevation of Tyrosine–Specific Phosphorylation in Human Gastric Cancer Cells," *Japan J. Cancer Res.*, 82:1428, 1991.

Talamonti, Curley, Gallick, Teeter, Kuo "Development and Progression of Human Colon Cancer," *Cancer Bull.*, 44:321, 1992.

Talamonti, Roh, Curley, Gallick, "Increase in Activity and Level of pp60$^{c-src}$ in Progressive Stages of Human Colorectal Cancer," *J. Clin. Invest.*, 91:53, 1993.

Talamonti, Roh, Curley, Gallick, "The c–src Oncogene Participates in the Development of Human Colorectal Liver Metastases," *Surg. Forum*, 42:422, 1991.

Termuhlen, Curley, Talamonti, Saboorian, Gallick, "Site–Specific Differences in pp60$^{c-src}$ Activity in Human Colorectal Metastases," *J. Surg. Res.*, 54:293, 1993.

Thompson and Ellman, "Synthesis and Applications of Small Molecule Libraries" *Chem. Rev.*, 96:555, 1996.

Thompson, Fry, Kraker, Denny, "Tyrosine Kinase Inhibitors. 2. Synthesis of 2,2'–dithiobis(1H–indole 3–alkanamides) and Investigation of Their Inhibitory Activity Against Epidermal Growth Factor Receptor and pp60$^{c-src}$ Protein Tyrosine Kinases" *J. Med. Chern.*, 37:598, 1994.

Waki, Kitanaka, Kamano, Tanaka, Kubota, Ohnishi, Takahara, Irino, "Antisense SRC Expression Inhibits U937 Human Leukemia Cell Proliferation in Conjuction with Reduction of c–MYB Expression," *Biochem. Biophys. Res. Commun.*, 201:1001, 1994.

Waksman, Kominos, Robertson, Pant, Baltimore, Birge, Cowbum, Hanafusa, Mayer, Overduin, Resh, Rios, Silverman, Kuriyan, "Crystal Structure of the Phosphotyrosine Recognition Domain SH2 of v–src Complexed with Tyrosine–Phosphorylated Peptides," *Nature*, 358:646, 1992.

Ward, Cook, Slater, Davies, Holdgate, Green, "Epidermal Growth Factor Receptor Tyrosine Kinase Investigation of Catalytic Mechanism, Structure–Based Searching and Discovery of a Potent Inhibitor," *Biochem. Pharm.*, 48:659, 1994.

Wong and Goldberg, "Kinetics and Mechanism of Angiotensin Phosphorylation by the Transforming Gene Product of Rous Sarcoma Virus," *J. Biol. Chem.*, 259:3127, 1984.

Yoneda, Lowe, Lee, Gutierrez, Niewolna, Williams, Izbicka, Uehara, Mindy, "Herbimycin a, A pp60$^{c-src}$ Kinase Inhibitor, Inhibits Osteoclastic nine Resorption in vitro and Hypercalcemia in vivo," *J. Clin. Invest.*, 91:2791, 1993.

Yu, Askalan, Keil II, Salter, "NMDA Channel Regulation by Channel–Associated Protein Tyrosine Kinase Src," *Science* 275:674, 1997.

Yuan, Jakes, Elliott, Graves, "A Rationale for the Design of an Inhibitor of Tyrosyl Kinase,". *J. Biol. Chem.*, 265:16205, 1990.

Zheng, Wang, Pallen, "Cell Transformation and Activation of pp60$^{c-src}$ by Overexpression of a Protein Tyrosine Phosphatase, *Nature*," 359:336, 1992.

L-Tyr, Bnz-Ph

D-Tyr, Bnz-Ph

L-Tyr, Bnz

INHIBITORS OF PROTEIN TYROSINE KINASES

The government owns rights in the present invention pursuant to grant numbers U01-CA53617 and R01 GM50353-01A from the National Institutes of Health.

BACKGROUND OF THE INVENTION

1. Field of the Invention

The present invention relates generally to the field of non-peptidyl inhibitors of protein tyrosine kinases. More particularly, the present invention concerns the inhibition of specific protein tyrosine kinases, for example pp60$^{c-src}$, and growth factor receptors such as the fibroblast growth factor receptor. The instant inhibitors are based on a 1,4-benzodiazepin-2-one nucleus. The invention further relates to the use of these inhibitors in situations where the inhibition of a protein tyrosine kinase is indicated.

2. Description of Related Art

Protein tyrosine kinases (PTKs) are a family of enzymes which transfer the γ-phosphate of ATP to the side chain of tyrosine residues on substrate proteins. There are three major classes of enzymes in this family. The first class to be identified were viral proteins, such as pp60$^{v-src}$ (the 60 kDa protein product of the viral src gene), which were capable of cell transformation. It was later discovered that these viral oncoproteins had normal cellular counterparts, for example pp60$^{c-src}$ (the 60 kDa protein product of the cellular src gene). These cellular proteins represent the second class of PTKs. The third class are represented by growth factor receptors, for example the fibroblast growth factor receptor (FGFr), the epidermal growth factor receptor (EGFr) and the platelet derived growth factor receptor (PDGFr).

PTKs are involved in a variety of different cellular processes. PTKs are often associated with cellular membranes and are involved in signal transduction and growth regulation. Alterations in the phosphorylation of PTK substrates are key events in cellular signaling.

Growth factor receptor tyrosine kinases are cell-surface proteins that receive information from outside the cell and convey it across the cell membrane. When a growth factor binds to its cognate receptor protein, the receptor is converted to an active form. The receptor then interacts with proteins on the inner surface of the cell membrane, altering their properties and/or subcellular location, resulting in changes in the behavior of the cell itself. These changes are many and various and may occur over the course of seconds (e.g., changes in ion flux), minutes (e.g., changes in cell shape), or hours (e.g., cellular mitosis).

Abberant levels, regulation and/or activity of a number of different PTKs play a key role in several human diseases. For example, pp60$^{c-src}$ (hereafter referred to as Src) is a PTK that is present in low levels, if at all, in normal eukaryotic cells (Barnekow, 1989; Punt et al., 1989). However, high concentrations and high activities of Src have been associated with numerous types of cancer. Breast cancer (Ottenhoff-Kalff et al., 1992; Partanen, 1994), stomach cancer (Takeshima et al., 1991), colon cancer (Rosen et al., 1986; Bolen et al., 1985, 1987; Cartwright et al., 1989, 1990; Talamonti et al., 1992, 1993; Termuhlen et al., 1993), hairy cell leukemia and a subgroup of B-cell lymphomas lymphomas (Lynch et al., 1993), low grade human bladder carcinoma (Fanning et al., 1992), and neuroblastoma (Bolen et al., 1985; O'Shaughnessy et al., 1987; Bjelfman et al., 1990) are all accompanied by greatly increased Src activity in the affected cells. Significantly, growth inhibition of several of these cancers has been correlated with decreases in Src activity, and for this reason, inhibitors of Src have excellent potential as anti-tumoral agents.

Other human cancers, e.g. melanoma, appear to be driven by an autocrine loop (Becker et al., 1989) comprising fibroblast growth factor (FGF) and its receptor (FGFr). As noted above, FGFr is a protein tyrosine kinase. An inhibitor of FGFr would therefore also be expected to have excellent potential as an anti-tumoral agent. Other serious diseases that have been linked with PTKs include osteoporosis, atherosclerosis, diabetic retinopathy, psoriasis, and possibly certain neurodegenerative disorders.

Inhibition of PTKs represents a promising avenue for treatment of disease. For example, Src is known to be involved with bone resorption (Hall et al., 1994), and it stands to reason that inhibition of Src would be an effective treatment modality in osteoporosis patents. Also, Src has recently been demonstrated to regulate the activity of N-methyl-D-aspartate (NMDA) ion channels (Yu et al., 1997) and NMDA-type glutamate channels in mammalian central neurons. Because dysfunction of NMDA receptor-mediated neurotransmission is believed to play a key role in the pathophysiology of Alzheimer's disease, Parkinson's disease (Coyle, et al. 1993), and schizophrenia (Heresco-Levy et al., 1996), this important discovery suggests that inhibition of Src may be helpful in the treatment of schizophrenia as well as other illnesses such as Parkinson's disease and seizure disorders that involve neural degeneration or abnormal regulation of NMDA channels.

There have been published reports of peptide-based inhibitors of PTKs. Various groups have substituted Phe or Phe analogues for Tyr in peptide substrates such as angiotensin II (Wong and Goldberg, 1984), epidermal growth factor receptor (EGFr) 1164–1176 (Honeggar et al., 1988), and insulin receptor (IR) 1142–1153 (Shoelson et al., 1989). Navarro et al. (1982) tested a series of peptidyl and amino acid halomethyl ketones as inhibitors of EGF-receptor kinase activity. Of nine compounds tested, only three showed significant inhibitory activity. Unfortunately, these investigators and others have found that peptides and oligonucleotides tend to have limited oral activities and rapid clearing times. Therefore, such materials have limited utility as bioavailable therapeutic agents. Thus, the development and characterization of non-peptidyl inhibitors of PTKs would represent a significant advance in the art.

Derivatives of 1,4-benzodiazepines have widespread biological activities and are one of the most important classes of bioavailable therapeutic agents (Sternbach, 1979). Benzodiazepine derivatives have been reported that are potent enzyme inhibitors, and that are agonists or antagonists, often with a high level of specificity and affinity. For example, 1,4-benzodiazepine derivatives have been described which are anxiolytic, anticonvulsant, and antihypnotic agents (Sternbach, 1979), selective cholecystokinin (CCK) receptor subtype A or B antagonists (Bock et al., 1989), K-selective opioid antagonists (Romer et al., 1982), platelet activating factor antagonists (Komecki et al., 1984), GP$_{IIbIIIa}$ inhibitors (Bondinell et al., 1993), and Ras farnesyl transferase inhibitors (James et al., 1993; Marsters et al., U.S. Pat. No. 5,532,359).

Unlike peptides, 1,4-benzodiazepines often have favorable pharmacokinetic properties such as good oral availability and long circulating half-lives. However, to date no suitable benzodiazepine inhibitors of PTKs have been described, and there are currently no specific potent small-molecule inhibitors of PTKs, such as Src, that have suitable pharmacokinetics, affinity, and specificity. Given the lack of inhibitors of protein tyrosine kinases with suitable properties, the development and characterization of non-peptidyl, small molecule inhibitors of PTKs would represent a significant contribution to the art.

SUMMARY OF THE INVENTION

The benzodiazepine inhibitors of the present invention overcome the problems described in the art. The benzodiazepine inhibitors of the present invention offer favorable pharmacokinetic properties and long circulating half-lives. The instant inhibitors are unique in that they do not contain catechol substituents and do not require manganese for potency as do some natural product-based inhibitors. This is significant in that catechol substituents are inherently chemically unstable toward oxidation, and many polyhydroxylated compounds (e.g., catechols) are especially unstable in the presence of manganese. This makes interpretation of structure-reactivity relationships and the development of selective inhibitors for PTKs difficult. In addition to moderate affinity, the instant inhibitors show some specificity for individual PTKs over a battery of other kinases and ATP-utilizing enzymes. These characteristics make the inhibitors of the present invention extremely useful in conditions where reduction of PTK activity is indicated.

In one embodiment, the present invention consists of benzodiazepine inhibitors represented by structural formula I:

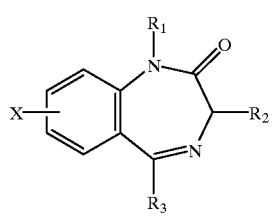

I $R_1$, $R_2$ and $R_3$ may each be independently described as Y bonded to W, where Y is a 0 to 6 atom straight or branched, saturated or unsaturated chain group comprising C, N, O or S, represented by:

Y=—[Q(m)$_p$]$_n$— where n 0 to 6,

Q may be C, N, O, S, or any combination of these atoms, wherein when Q is O or S, p is 0, and when Q is N or C, p is 0, 1 or 2, and and m may be no substituent or any of the following:

H, OH, SH, $NH_2$, halogen, cyano group, nitro, carbonyl oxygen, carboxyl group, sulfonyl group, k-$CH_3$,
k-$CH_2CH_3$,
k-$CH_2CH_2CH_3$, or
k-$CH(CH_3)_2$, where k=no substituent, O or S;

W may be hydrogen or any three membered, four membered, five membered, six membered or fused bicyclic ring system comprising C, N, O or S, represented by

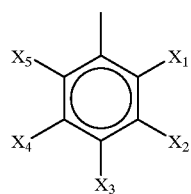 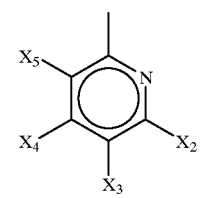

-continued

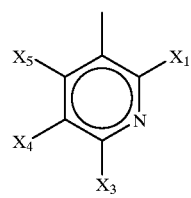 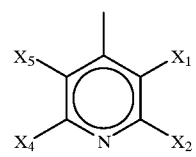

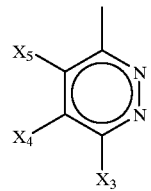 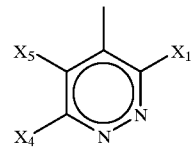

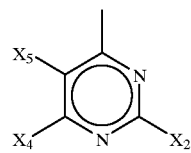 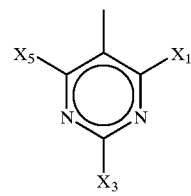

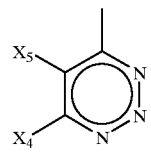 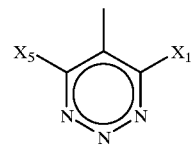

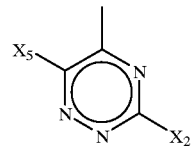 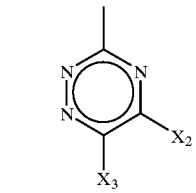

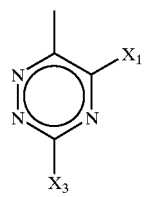 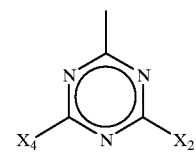

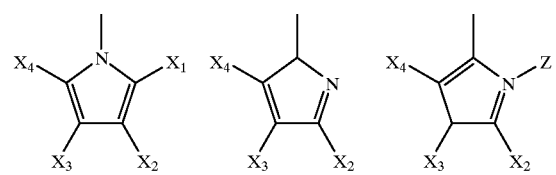

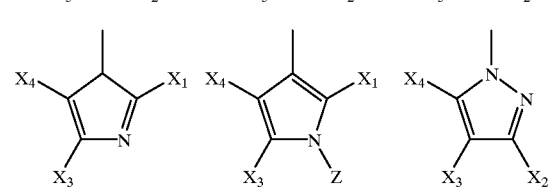

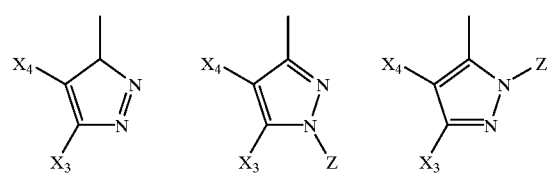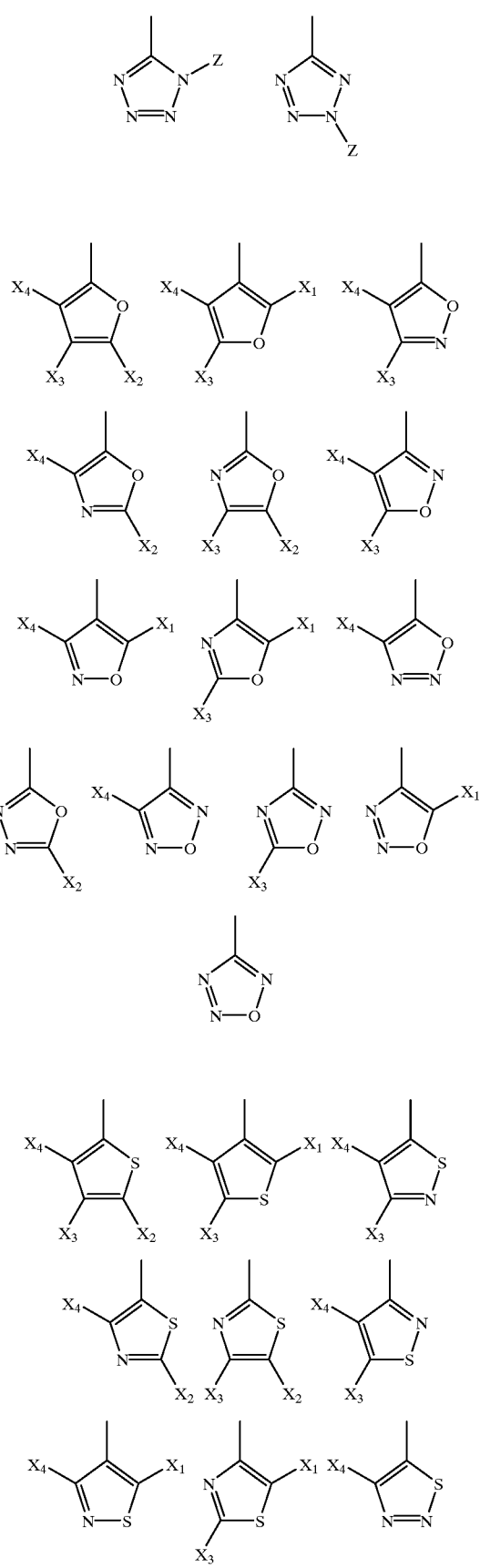

-continued

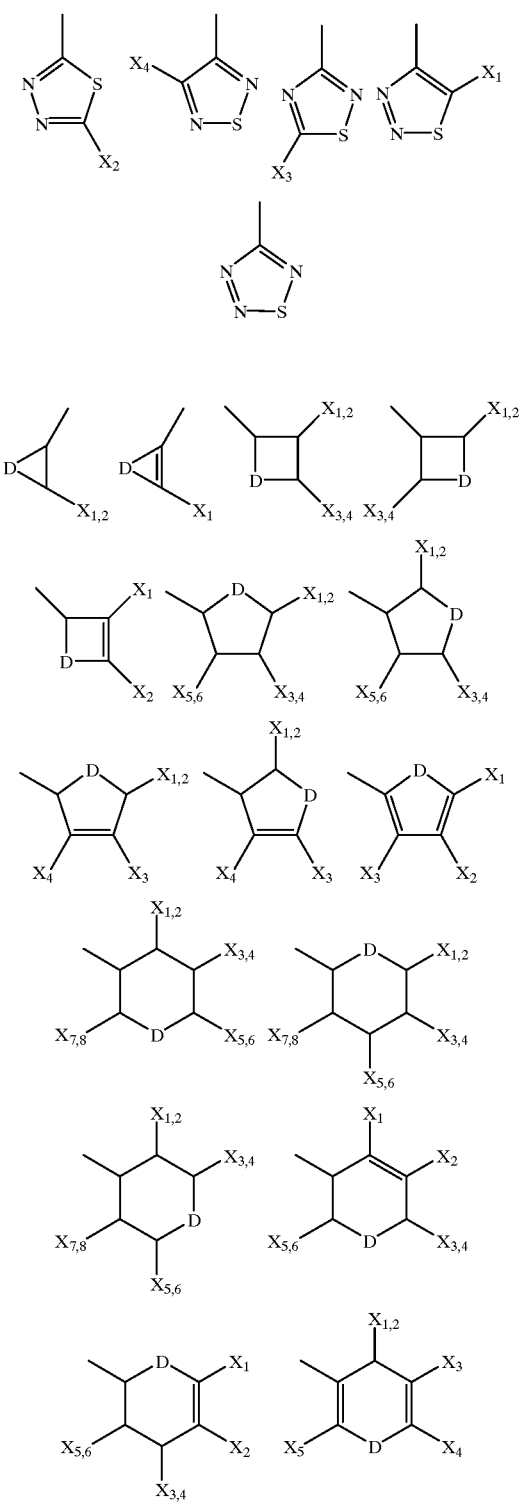

X and and $X_1$–$X_8$ are separately and independently selected from hydrogen; halogens; alkyl, aryl, or acyl; carboxyl, sulfonyl, nitro, or boronyl groups; —O—$R_4$, where $R_4$ is a hydrogen, or an alkyl, aryl, or acyl group; —S—$R_4$, where $R_4$ is a hydrogen, or an alkyl, aryl, or acyl group; —S(O)—$R_5$, where $R_5$ is an alkyl or aryl group; —SO$_2$—$R_5$, where $R_5$ is an alkyl or aryl group; —SO$_2$(NR$_4$)$_2$, where $R_4$ is a hydrogen, or an alkyl or aryl group; -cyano group; —N(R$_4$)$_2$, where $R_4$ is a hydrogen, or an alkyl, aryl, or acyl group or a combination of these; —N(R$_6$)$_3$, where $R_6$ is a hydrogen, or an alkyl or aryl group; and —C(R$_4$)$_2$T, where $R_4$ is a hydrogen, or an alkyl, aryl, or acyl group;

T may be separately and independently selected from hydrogen; halogens; alkyl, aryl, or acyl; carboxyl, sulfonyl, nitro, or boronyl groups; —O—$R_4$, where $R_4$ is a hydrogen, or an alkyl, aryl, or acyl group; —S—$R_4$, where $R_4$ is a hydrogen, or an alkyl, aryl, or acyl group; —S(O)—$R_5$, where $R_5$ is an alkyl or aryl group; —SO$_2$—$R_5$, where $R_5$ is an alkyl or aryl group; —SO$_2$(NR$_4$)$_2$, where $R_4$ is a hydrogen, or an alkyl or aryl group; -cyano group; —N(R$_4$)$_2$, where $R_4$ is a hydrogen, or an alkyl, aryl, or acyl group or a combination of these; —N(R$_6$)$_3$, where $R_6$ is a hydrogen, or an alkyl or aryl group;

Z may be separately and independently selected from hydrogen; alkyl, aryl, amino, nitro, or halogen groups; D may be separately and independently selected from carbon, nitrogen, sulfur, or oxygen; $R_4$ may be hydrogen, or alkyl, aryl, or acyl groups; $R_5$ may be alkyl or aryl groups; $R_6$ may be hydrogen, or alkyl or aryl groups; and salts of these compounds.

In one aspect, the compounds of the present invention may have a Y group of $R_2$ wherein at least one atom is present. It will be recognized that, in this aspect, the compounds of the present invention may comprise a racemic mixture of enantiomers. In certain aspects of the invention, preferred compounds are those which are substantially free of their diastereomer. In particular embodiments the preferred compounds are those having the R configuration about the 3-carbon of the seven member ring. In alternative aspects, preferred compounds are those having the S configuration about the 3-carbon of the seven member ring.

A particularly preferred compound in particular aspects of the present invention is one in which $R_1$ is —CH$_2$C$_6$H$_4$C$_6$H$_5$, $R_2$ is —CH$_2$C$_6$H$_4$OH, $R_3$ is p-phenol, and X is 7-Cl, wherein the compound has the R configuration about the 3-carbon of the seven member ring. In other aspects, the preferred compound is one in which $R_1$ is —CH$_2$C$_6$H$_4$C$_6$H$_5$, $R_2$ is —CH$_2$C$_6$H$_4$OH, $R_3$ is p-phenol, and X is 7-Cl, wherein the compound has the S configuration about the 3-carbon of the seven member ring. In further aspects, the preferred compound is one in which $R_1$ is —CH$_2$C$_6$H$_5$, $R_2$ is —CH$_2$C$_6$H$_4$OH, $R_3$ is p-phenol, and X is 7-Cl, wherein the compound has the S configuration about the 3-carbon of the seven member ring.

It is contemplated that the compounds herein disclosed may be formulated into pharmaceutical compositions comprising any known pharmaceutically acceptable excipients, as described in detail hereinbelow. These pharmaceutical compositions may be administered, for example, parenterally, orally, topically, intravenously, intramuscularly, sub-cutaneously, or intraperitoneally.

The present invention also provides methods of inhibiting a protein tyrosine kinase comprising contacting the protein tyrosine kinase with an effective inhibitory amount of one or more of the instant compounds. The protein tyrosine kinases which may be inhibited by the methods and compounds of the present invention include, but are not limited to, pp60$^{Src}$, fibroblast growth factor receptor (FGFr), epidermal growth factor receptor (EGFr), platelet derived growth factor receptor (PDGFr), C-Src kinase (Csk), Lck, and Abl.

In certain embodiments, the protein tyrosine kinases inhibited by the compounds and methods of the present invention are located in a cell, and the inhibitory compounds of the present invention are provided to the cell. In further aspects the cell may be located in a mammal, and in these embodiments, a pharmaceutically acceptable form of the instant compounds is administered to the mammal. In yet other aspects, the mammal may be a human, and in these, a pharmaceutically acceptable form of the instant compounds is administered to a human subject.

The present invention further provides methods of inhibiting a protein tyrosine kinase wherein a biologically effective amount of a pharmaceutical composition comprising at least one of the instant compounds is administered to a mammal. It is contemplated that the instant method of administering the biologically effective amount of the instant pharmaceutical composition to a mammal may inhibit diseases including, but not limited to, atherosclerosis, angiogenesis, osteoporosis, diabetic retinopathy, and the proliferation of tumor cells the proliferation of tumor cells in the mammal. The invention also provides methods of inhibiting diseases characterized by abnormal NMDA channel regulation in the mammal; such diseases include, but are not limited to, Alzheimer's disease, Parkinson's disease, seizures and seizure disorders and schizophrenia. The invention further provides methods of inhibiting abnormal cellular proliferation in the mammal. In certain embodiments, the mammal is a human subject.

The present invention additionally provides methods of treating cancer in mammals, including humans, wherein a therapeutically effective inhibitory amount of a pharmaceutically acceptable composition comprising one or more of the instant compounds is administered to the mammal. In certain aspects, the compositions may be injected into a tumor. The instant methods involve treating cancers including, but not limited to breast cancer, stomach cancer, colon cancer, hairy cell leukemia, certain B-cell lymphomas, low grade bladder carcinoma, neuroblastoma, and non-small cell lung carcinoma. In certain aspects of the present invention, an effective amount of one or more of the instant compositions is administered in combination with an effective amount of one or more traditional chemotherapeutic compounds, such as those disclosed in Section VIII hereinbelow, except those combinations that may be contraindicated.

The present invention also provides methods of treating disesases characterized by abnormal NMDA channel regulation in mammals, including humans, wherein a therapeutically effective inhibitory amount of a pharmaceutically acceptable composition comprising one or more of the instant compounds is administered to the mammal. The instant methods involve treating diseases including, but not limited to Alzheimer's disease, Parkinson's disease, seizures and seizure disorders, and schizophrenia. In certain aspects of the present invention, an effective amount of one or more of the instant compositions is administered in combination with an effective amount of one or more compounds traditionally employed in the treatment of diseases characterized by abnormal NMDA channel regulation, except those combinations that may be contraindicated.

It is contemplated for purposes of the present invention that effective dosages of the instant protein tyrosine kinase inhibitor drugs may range from as low as about 1 mg per day to as high as about 1000 mg per day, including all intermediate dosages therebetween. It will be readily understood that "intermediate dosages", in these contexts, means any dosages between the quoted ranges, such as about 1, 2, 3, 4, 5, 6, 7, 8, 9, 10, etc.; 12. 13, 14, etc.; 27, 28, 29, 30, etc; 37, 38, 39, 40, etc.; 47, 48, 49, 50, etc; 57, 58, 59, 60, etc.; 100, 101, 102, 103, 104, etc.; 500, 501, 502, 503, etc.; 600, 700, 800, 900, and about 1000 mg per day, including all fractional dosages therebetween.

More preferably, effective dosages of the instant protein tyrosine kinase inhibitor drugs may range from about 10 mg per day to about 100 mg per day, including all intermediate dosages therebetween. It will be readily understood that "intermediate dosages", in these contexts, means any dosages between the quoted ranges, such as about 10, 11, 12, 13, 14, etc.; 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, etc.; and about 100 mg per day, including all fractional dosages therebetween. Of course, all of these dosages are exemplary, and any dosage in between these points is also expected to be of use in the invention.

By "about" is meant "approximately" or "in the vicinity of." For example, the phrase "about 100"may mean 101, 102, 103, 104, etc., and fractional values therebetween, and it may also mean 95, 96, 97, 98, 99, etc., and fractional values therebetween.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
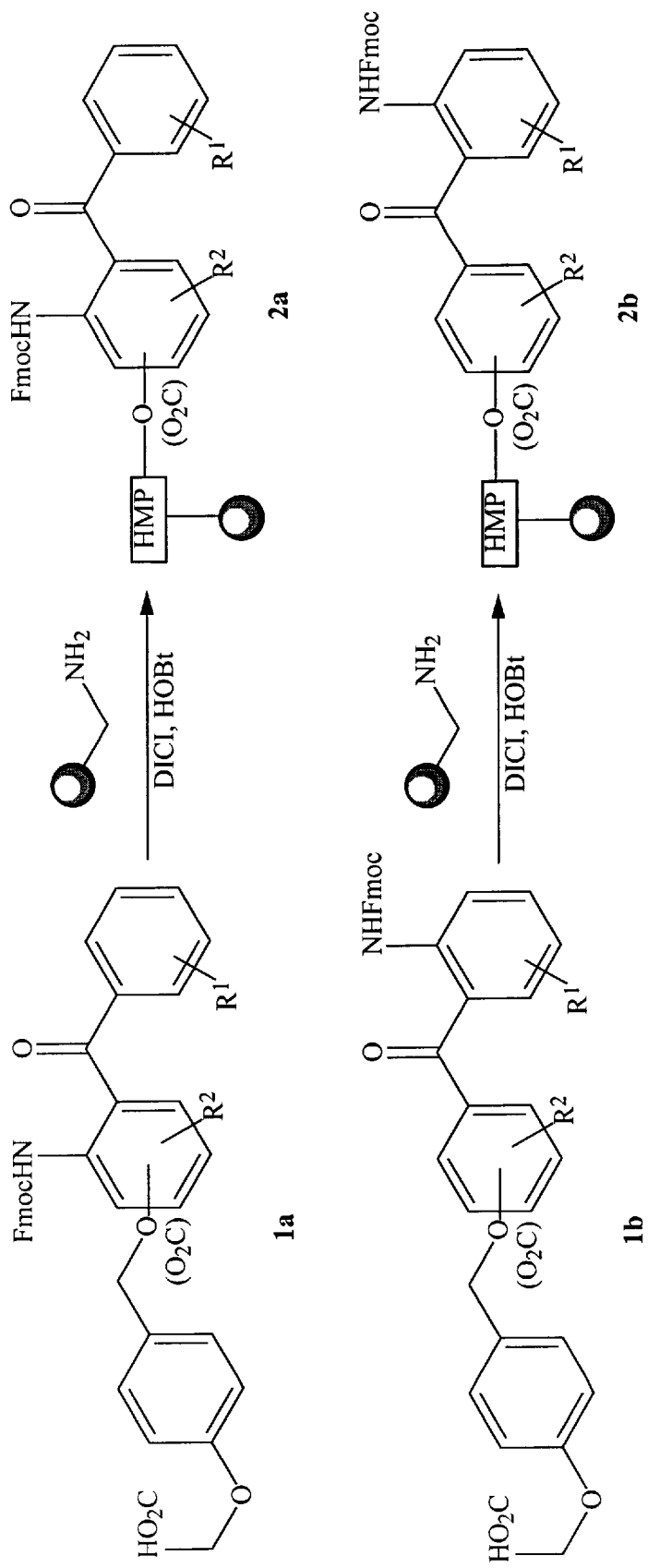
FIG. 1 shows schematically the derivatization of solid support with protected 2-aminobenzophenones.

Protein tyrosine kinases (PTKs) catalyze the transfer of the γ-phosphate of ATP to protein substrates within the cell. PTKs are often associated with cellular membranes and are involved in signal transduction and growth regulation pathways. Alterations in the phosphorylation of PTK substrates are key events in cellular signaling.

The benzodiazepine-based inhibitors of the present invention act by blocking this transfer of phosphate thereby inhibiting the catalytic activity of PTKs. These compounds are reversible inhibitors which exhibit a "mixed" type of inhibition (i.e., they affect both the $K_m$ and $V_{max}$ values) against both ATP and protein substrates. Studies with C-Src kinase (Csk) deletion mutants have indicated that these compounds inhibit by binding to the catalytic domain of PTKs. Catalytically active mutants devoid of the SH2 or SH3 domain were found to equally inhibit the kinase activity of Csk, suggesting that they bind to the SH1, or catalytic domain.

I. Definitions

As used herein, the following terms are intended to have the following general meanings:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.

2. Ligand: A ligand is a molecule that is recognized by a particular receptor or binding protein.

3. Benzodiazepines: A seven-membered organic ring with two nitrogens in the ring, normally with nitrogens at positions 1 and 4, often with an aromatic ring attached to the seven-membered ring, normally at positions 6 and 7. Benzodiazepines include compounds having a 5-phenyl-3H-1,4-benzodiazepin-2-(1H)-one nucleus, including those with substitutions at the 1-, 3-, 5- and 6- through 9-positions. Many of these compounds will have a phenyl ring at the 5-position, thereby resulting in two phenyl rings in the structure, both optionally substituted.

4. Receptor: A molecule that has an affinity for a given ligand. Receptors may be naturally-occurring or synthetic molecules. Also, they can be employed in their unaltered state or as aggregates with other species. Receptors may be attached, covalently or non-covalently, to a binding member, either directly or via a specific binding substance. Receptors are sometimes referred to in the art as anti-ligands. As the term receptors is used herein, no difference in meaning is intended. A "Ligand Receptor Pair" is formed when two macromolecules have combined through molecular recognition to form a complex.

5. Protecting group: A material which is chemically bound to a monomer unit and which may be removed upon selective exposure to an activator such as a selected chemical activator such as an acidic or basic environment, or to another selected activator such as electromagnetic radiation and, especially light, such as ultraviolet and visible light. Examples of protecting groups with utility herein include those comprising fluorenylmethyloxycarbonyl, nitropiperonyl, pyrenylmethoxycarbonyl, nitroveratryl, nitrobenzyl, and other orthonitrobenzyl groups, dimethyl dimethoxybenzyl, 5-bromo-7-nitroindolinyl, o-hydroxy-alpha-methyl cinnamoyl, and 2-oxymethylene anthraquinone.

6. Substantially Pure: A molecule such as a benzodiazepine is considered to be "substantially pure" within a predefined region of a substrate when it exhibits characteristics that distinguish it from molecules in other predefined regions. Typically, purity will be measured in terms of biological activity or function as a result of uniform composition. Such characteristics will typically be measured by way of binding with a selected ligand or receptor. Preferably the region is sufficiently pure such that the predominant species in the predefined region is the desired molecule. According to preferred aspects of the invention, the molecules synthesized on the pin or other structure are 5% pure, more preferably more than 10% pure, preferably more than 20% pure, more preferably more than 80% pure, more preferably more than 90% pure, more preferably more than 95% pure, where purity for this purpose refers to the ratio of the number of desired ligand molecules formed in a predefined region to the total number of molecules formed in the predefined region.

7. Activator: A material such as a chemical or energy source adapted to render a group active and which is directed from a source to a predefined location on a substrate, such as radiation. A primary illustration of an activator is light such as visible, ultraviolet or infrared light. Other examples of activators include ion beams, electric fields, magnetic fields, electron beams, x-ray, and the like.

8. Combinatorial Synthesis Strategy: An ordered strategy for parallel synthesis of diverse chemical structures polymer sequences by sequential addition of reagents and which may normally be represented by a reactant matrix, and a switch matrix, the product of which is a product matrix. A reactant matrix is a 1 column by m row matrix of the building blocks to be added, where 1 and m are integers indicating the numbers of rows and columns, respectively, of the matrix. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other deprotecting or activating agents to remove protecting groups from materials for addition of other materials such as amino acids. In some embodiments, selected columns of the switch matrix are arranged in order of increasing binary numbers in the columns of the switch matrix. Such strategies and the representational notation therefor are discussed in Fodor et al., (1991).

9. Linker: A molecule or group of molecules attached to a substrate and spacing a synthesized polymer from the substrate, such as for exposure/binding to a receptor.

10. Alkyl: A cyclic, branched, or straight-chain aliphatic group containing only carbon and hydrogen. This term is further exemplified by groups such as methyl, heptyl, $(CH_2)_2$, and adamantyl. Alkyl groups can either be unsubstituted or substituted with one or more non-interfering substituents, e.g., halogen, alkoxy, acyloxy, hydroxy, mercapto, carboxy, benzyloxy, phenyl, or benzyl, each optionally substituted with additional non-interfering substituents. The term "non-interfering" characterizes the substituents as not adversely affecting any reactions to be performed in accordance with the process of this invention.

11. Lower alkyl: An alkyl group of one to six carbon atoms. Lower alkyl groups include, but are not limited to, those exemplified by methyl, ethyl, n-propyl, iso-propyl, n-butyl, tert-butyl, iso-butyl (2-methylpropyl), cyclopropylmethyl, iso-amyl, n-amyl and hexyl. Preferred lower alkyls are methyl and ethyl. If more than one alkyl group is present in a given molecule, each may be independently selected from "lower alkyl" unless otherwise stated.

12. Aryl: A monovalent unsaturated aromatic carbocyclic group having a single ring (e.g., phenyl) or multiple condensed rings (e.g., naphthyl or anthryl), which can optionally be unsubstituted or substituted with hydroxy, lower alkyl, alkoxy, chloro, halo, mercapto, or other non-interfering substituents.

13. Heteroaryl or HetAr: A monovalent unsaturated aromatic carbocyclic group having a single ring (e.g., pyridyl or furyl) or multiple condensed rings (e.g., indolizinyl or benzo[b]thienyl) and having at least one hetero atom, such as N, O or S, within the ring, which can optionally be unsubstituted or substituted with hydroxy, alkyl, alkoxy, halo, mercapto, and other non-interfering substituents.

14. Arylalkyl: The groups -R"-Ar and -R"-HetAr, where Ar is an aryl group, HetAr a heteroaryl group, and R" is straight-chain or branched-chain aliphatic group. Examples of arylalkyl groups include the sidechains of the amino acids phenylalanine and tryptophan.

15. Carboxyalkyl refers to the group —C(O)—R", where R" is lower alkyl.

16. Acyloxy refers to the group —OC(O)R", where R" is alkyl.

17. Monomer: A molecule which is not substantially comprised of repeating molecular subunits.

II. Protein Tyrosine Kinases

Inhibition of PTKs represents a promising avenue for treatment of disease. The present invention provides compounds that can inhibit one or more PTK(s). PTKs contemplated for inhibition by the instant compositions include, but are not limited to, those described below.

A. Src

Src is a protein tyrosine kinase (PTK) associated with cellular membranes and is involved in signal transduction and growth regulation pathways. Alterations in the phosphorylation of Src substrates are key events in cellular signaling. Most normal cells contain very low levels and activity of Src (Barnekow, 1989; Punt et al., 1989) and the enzyme is not required for the establishment or maintenance of cell viability (Soriano et al., 1991).

However, Src activity is greatly increased in many human cancers: breast cancer (Ottenhoff-Kalff et al., 1992; Partanen, 1994), stomach cancer (Takeshima et al., 1991), colon cancer (Rosen et al., 1986; Bolen et al., 1985, 1987; Cartwright et al., 1989, 1990; Talamonti et al., 1992, 1993; Termuhlen et al., 1993), hairy cell leukemia and a subgroup of B-cell lymphomas (Lynch et al., 1993), low grade human bladder carcinoma (Fanning et al., 1992), neuroblastoma (Bolen et al., 1985; O'Shaughnessy et al., 1987; Bjelfman et al., 1990), and, based on cell culture studies, probably non-small cell lung carcinoma (Budde et al., 1994a). In the case of colon cancer, Src is activated more frequently than ras or p53 (reviewed by Jessup and Gallick, 1993), and undergoes two distinct activations corresponding with malignant transformation of colonocytes (Cartwright et al., 1990) and tumor progression (Talamonti et al., 1991, 1992; Termuhlen et al., 1993).

Antisense to src inhibits growth of human monoblastoid leukemia (Waki et al., 1994), K562 human leukemia cells (Kitanaka et al., 1994) and HT-29 human colon cancer cells (Staley et al., 1995). In addition, growth inhibition of colon tumor (Garcia et al., 1991; Novotny-Smith and Gallick, 1992) and neuroblastoma cell lines (Preis et al., 1988) correlates with decreases in tyrosine kinase activity of Src. Changes in Src activity are associated with changes in the cell cycle (Chackalaparampil and Shalloway, 1988) and alterations in the regulation of Src activity have been associated with neoplasia (Bolen et al., 1987, 1995; Zheng et al., 1992; Sabe et al., 1992). Therefore, drugs developed against Src will have the advantage of limited or no systemic toxicity but high specificity for tumors shown to have elevated activity of this PTK.

In addition to their potential as anti-tumor agents, Src inhibitors have potential for treatment of osteoporosis, a condition in which bone resorption is increased resulting in weakening of bone. It was shown that mice depleted of the Src gene developed osteopetrosis (Soriano et al., 1991), and that Src is involved with bone resorption (Hall et al., 1994). Herbimycin A, a Src inhibitor, inhibits osteoclastic bone resorption in vivo (Yoneda et al., 1993). Inhibition of Src would be an effective treatment modality in osteoporosis patients.

Src has recently been demonstrated to regulate the activity of N-methyl-D-aspartate (NMDA) ion channels (Yu et al., 1997) and NMDA-type glutamate channels in mammalian central neurons. Because disfunction of NMDA receptor-mediated neurotransmission is believed to play a key role in the pathophysiology of Alzheimer's disease, Parkinson's disease (Coyle, et al. 1993), and schizophrenia (Heresco-Levy et al., 1996), this important discovery suggests that inhibition of Src may be helpful in the treatment of schizophrenia as well as other illnesses involving neural degeneration or abnormal regulation of NMDA channels.

Inhibition of Src would have the effect of interrupting the signal transduction pathways in which it participates and would thereby reduce the rate of growth of cancer cells. There are a number of potential sites in Src for targeting inhibitors. The SH2 and SH3 domains are involved in interactions with other proteins (Waksman et al., 1992; Luttrell et al., 1994), and the phosphoryl transfer site (SH1 domain) is the active site of the enzyme. Compounds binding to SH2 and SH3 domains would block the protein—protein interactions and the recruitment of other signal transduction proteins mediated by these domains. However, because many other important cellular proteins may also have SH2 and/or SH3 domains, it may be difficult to design specific inhibitors of SH2 or SH3 domains.

Active-site directed inhibitors could be targeted to the ATP binding site, the protein substrate binding site, or both (bisubstrate analogues). Although examples of ATP-competitive inhibitors selective for Src over protein kinase A (Dow et al., 1994) or EGF-receptor over other PTKs (Fry et al., 1994) have been reported, inhibitors directed at the ATP binding site have the potential of interaction with ATP binding sites on large number of other kinases and ATP utilizing enzymes required for general metabolism. This potential lack of selectivity could lead to increased toxicity. Furthermore, drugs that have a competitive mechanism of inhibition against ATP have lower potency in situ, compared to their in vitro $K_i$ values, due to the saturating concentration of ATP within the cell.

The gene encoding Src has been cloned. Recombinant Src was prepared by expression in the baculovirus-insect cell system, and purified as published (Budde et al., 1993).

B. Growth Factor Receptors

There have been published reports of peptide-based inhibitors of PTKs. Various groups have substituted Phe or Phe analogues for Tyr in peptide substrates such as angiotensin II (Wong and Goldberg, 1984), epidermal growth factor receptor (EGFr) 1164–1176 (Honeggar et al., 1988), and insulin receptor (IR) 1142–1153 (Shoelson et al., 1989), and have used these to probe phosphorylation kinetics. Observed binding constants paralleled $K_m$ values, 0.1–4 mM. Yuan et al. (1990) substituted monofluorotyrosine as well as both enantiomers of tetrafluorotyrosine in a gastrin analogue. Against the insulin receptor tyrosine kinase, the $K_m$ of the parent gastrin was 400 $\mu$M whereas the $K_m$ of the monofluoro analogues was 100 $\mu$M. The $K_i$ of the L-tetrafluorotyrosine analogue was 4 $\mu$M and the $K_i$ of the D-diastereomer was 20 $\mu$M. The conclusion was that increased fluorination of the aromatic ring lowered the $pK_a$ of the Tyr hydroxyl and the increased negative charge of the phenolic side chain resulted in increased interaction with the enzyme. However, as discussed above, peptide-based inhibitors have limited bioavailability and rapid clearing times.

Navarro et al. (1982) tested a series of peptidyl and amino acid halomethyl ketones as inhibitors of EGF-receptor kinase activity. Of nine compounds tested, only three showed significant inhibitory activity, suggesting that the mode of inhibition was not due to nonspecific alkylation of the enzyme. However, these investigators did not determine which residues of the EGF-receptor were alkylated. Cushman et al. (1990) incorporated b-(4-pyridyl-1-oxide)-alanine into angiotensin I. On phosphorylation, this potential "suicide substrate" is proposed to become an electrophile hypothesized to react with a nucleophile within the enzyme. The peptide was a weak competitive inhibitor ($K_i$=2 mM) and no time-dependent inactivation was observed.

The problems with peptide-based inhibitors have led to the search for non-peptidyl inhibitors of PTKs. Over the past few years, several non-peptidyl inhibitors isolated from natural products have been identified, including lavendustin A, piceatannol, erbstatin, quercetin, genistein, and herbimycin A (reviewed by Chang and Geahlen, 1992; Burke, 1992). From these the polyhydroxylated phenyl and styryl groups of erbstatin and piceatannol, and the salicyl group of lavendustin A have been identified as pharmacophores and several groups have carried out structure activity studies of molecules possessing these features (Burke, 1993, 1994; Chen et al., 1994; Cushman et al., 1991 a, b, c; Dow et al., 1994; Fry et al., 1994; Maguire et al., 1994; Thompson et al., 1994). The small molecule inhibitors tend to compete with ATP binding and show low specificity for individual PTKs. Typically, these inhibitors exhibit $IC_{50}$ or $K_i$ values in the low $\mu M$ range for a variety of PTKs, the exceptions being PD153035 (4-(3-bromophenylamino)-6,7-dimethoxyquinazoline) of Fry et al., (1994) which has a $K_i$ of 5 pM for EGFR kinase activity, and CAQ (4-(3-chlorophenylamino)-quinazoline), which has a $K_i$ value between 16 and 32 nM (Ward et al., 1994). Unfortunately, many small molecule inhibitors may suffer from reduced efficacy in vivo. This may be due to the fact that these small molecule inhibitors are competing directly with the saturating concentration of ATP within the cell.

The genes encoding Csk, Lck, Abl, and the FGF receptor have all been cloned. The genes encoding Csk, Abl, and the FGF receptor were cloned from humans, and the genes encoding Lck were cloned from a mouse. Recombinant Csk, Lck, Abl, and the FGFr were expressed as glutathione-S-transferase fusion proteins using the pGEX expression vector and *E. coli*, and purified as described (Sun et al., 1995).

III. General Methods of Inhibitor Synthesis

One application of the present invention is the preparation and screening, preferably in parallel and simultaneous fashion, of large numbers of benzodiazepine derivatives as inhibitors of PTKs. Benzodiazepines are useful drugs for the targeting of enzymes, regulatory proteins and receptors of various kinds, and a variety of benzodiazepines, as well as their binding affinities, are known. Many more benzodiazepine structures may be postulated, however, and considered as potential active drugs for the same target species, and benzodiazepines as well as other drugs which target other enzymes, regulatory proteins and receptors are often sought.

To achieve the preparation and screening of large numbers of compounds that have benzodiazepine structures and which inhibit PTKs, the present disclosure provides solid-phase synthesis methods for benzodiazepines in which variable substituent groups are attached to a common central benzodiazepine structure. In one aspect of the solid-phase synthesis methods, a benzodiazepine precursor which contains a phenyl ring of the benzodiazepine without the closed heterocyclic ring is bonded to a solid support through a linkage on the phenyl ring. Either phenyl ring of the benzophenone system may be bonded to the solid support. Once the precursor is bonded to the solid support, a series of reactions is performed by contacting the solid support with a series of liquid-phase reagents. These reactions include closure of the heterocyclic ring and derivatization of the compound at various locations on the rings or other reactive sites on the compound structure. Appropriate protecting group(s) are attached to the precursor prior to the reaction with the solid support and to various sites on the molecule and the reagents to ensure that the desired reaction in each case occurs at the desired location on the structure.

This solid-phase synthesis permits each reaction to be confined to the surface area of a small solid structure. The physical joining of a multitude of small solid structures into a single unit, for example, then permits the simultaneous handling of a multitude of compounds and reagents. The use of structures of this kind for certain multiple simultaneous reactions is known in the art, and its application to the present invention will become apparent from the description which follows.

A. Abbreviations

In the schemes and examples below, the following standard abbreviations are employed.

| | |
|---|---|
| DMF | dimethylformamide |
| NMP | 1-methyl-2-pyrrolidinone |
| FAB | fast atom bombardment |
| HPLC | high pressure liquid chromatography |
| HMP | 4-hydroxymethylphenoxyacetic acid |
| PyBOP | benzotriazole-1-yl-oxy-tris-pyrrolidino-phosphonium hexafluorophosphate |
| HOBt | 1-hydroxybenzotriazole hydrate |
| MALDI-MS | matrix-assisted laser desorption ionization mass spectroscopy |
| MeOH | methanol |
| THF | tetrahydroturan |
| DMSO | dimethylsulfoxide |
| NMR | nuclear magnetic resonance |
| DICI | diisocarbodiimide |
| AcOH | acetic acid |
| TFA | trifluoroacetic acid |
| $Me_2S$ | dimethylsulfide |

B. Solid-Phase Synthesis of 1,4-Benzodiazepines

In the construction and evaluation of a library of 1,4-benzodiazepine derivatives several criteria should be met. (i) The benzodiazepine derivatives should be synthesized on a solid support for the same reason that it has been employed for all of the chemical approaches for the synthesis and evaluation of peptide libraries, i.e., the isolation of support-bound reaction products is accomplished simply by washing non-covalently bound reagents away from the support, making it straightforward to drive reactions to completion by the use of excess reagents. (ii) The variable components, or building blocks, used for the synthesis of a benzodiazepine library should be readily synthesized or (ideally) commercially available. This greatly expedites the process of library synthesis since time is not consumed in the repetitive synthesis of different building block derivatives. (iii) After syntheses of the compounds are complete, the compounds should be removed from the support so that the compounds can be assayed in solution because the solid support may complicate or interfere with protein binding to the support-bound small molecule.

According to these criteria the inventors initially prepared the 1,4-benzodiazepines from three components:

2-aminobenzophenones, amino acids and alkylating agents. Substituted 2-N-Fmoc-aminobenzophenones are coupled to the acid cleavable 4-hydroxymethylphenoxyacetic acid (HMP) linker using solution chemistry. As shown in FIG. 1, the linker may be attached through a hydroxyl or carboxyl group located on either aromatic ring of the 2-aminobenzophenone. The linker derivatized aminobenzophenones 1 of FIG. 1 are then coupled to the solid-support by standard amide bond forming methods.

Synthesis of benzodiazepine derivatives on solid support (FIG. 2) is initiated by removal of the Fmoc protecting group from 2 by treatment with piperidine in DMF. An α-N-Fmoc amino acid is then coupled to the deprotected 2-aminobenzophenone. Standard activation methods for solid-phase peptide synthesis were not successful for this coupling step due to the poor basicity and nucleophilicity of 2-aminobenzophenones. However, the activated α-N-Fmoc-amino acid fluorides developed by Carpino et al., (1990) couple efficiently to provide the amide products 3 even for electron deficient 2-aminobenzophenone derivatives. The Fmoc protecting group is then removed using piperidine in DMF, and the resulting free amine is treated with 5% acetic acid in NMP or DMF at 60° C. to provide the benzodiazepine derivatives 4 that incorporate two of the three components for introducing diversity.

Figure 3:
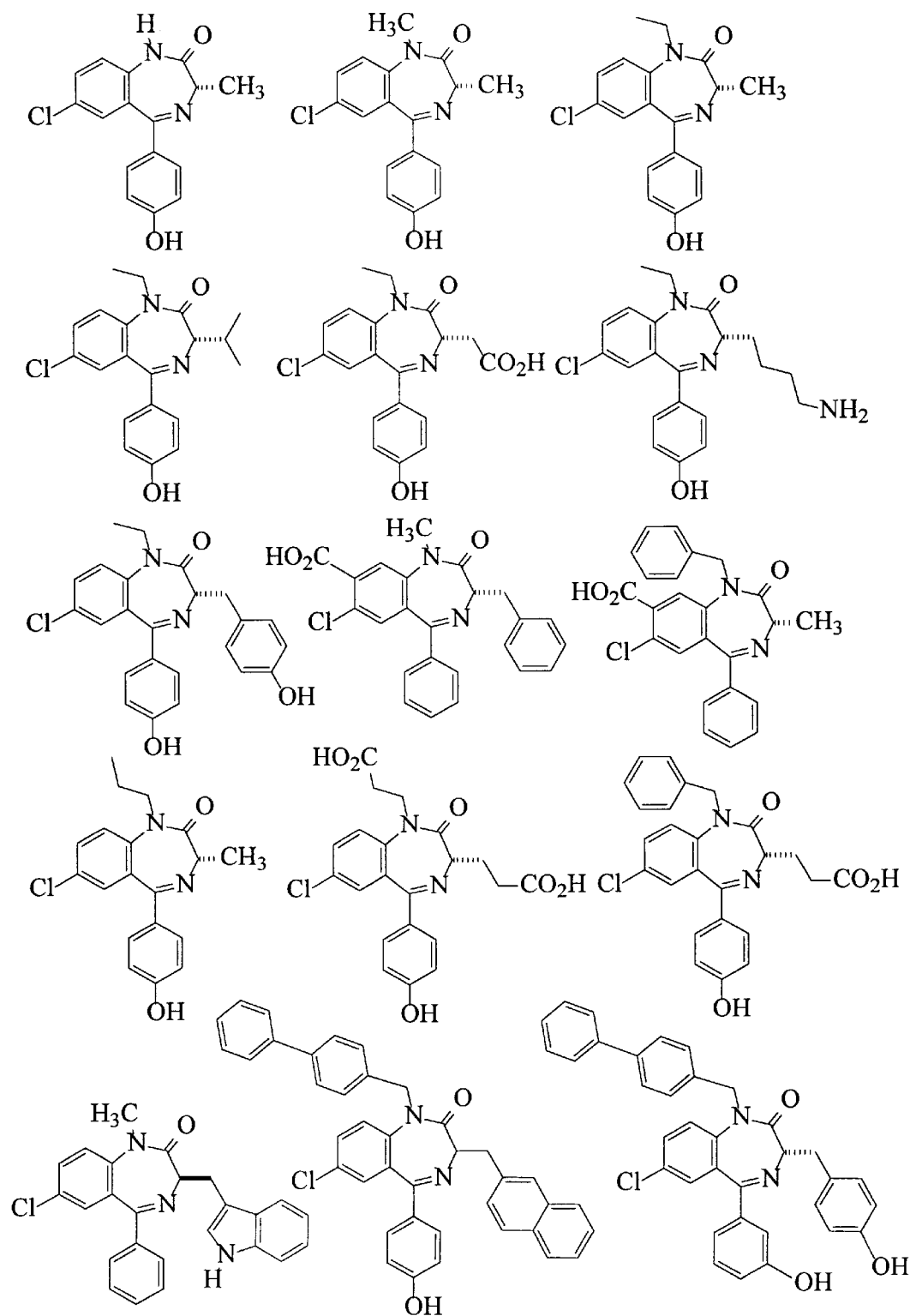
FIG. 3 shows structures of representativer 1,4-benzodizepine derivatives prepared by the route of FIG. 2. The average yield for derviatives shown is 90%, based upon the the initial 2-aminobenzophenone loading level of the resin.

Alkylation of the anilide of 4 provides the fully derivatized 1,4-benzodiazepines S. In order to ensure complete reaction on a solid support excess reagent is generally employed. Therefore, either lithiated 5-phenylmethyl-2-oxazolidinone or lithiated acetanilide was employed as the base since they are basic enough to completely deprotonate the anilide of 4. Excess reagent will not deprotonate other functionality that may be present in the benzodiazepine structure such as amide, carbamate, or ester functionality. Treatment with the volatile acid cleavage cocktail trifluoroacetic acid/dimethyl sulfide/H$_2$O (85:10:5) then affords the benzodiazepine products 6, which are obtained in high yield (85–100%) after chromatography based on the support-bound starting material 2. Finally, no racemization (<1%) of selected derivatives was detected as determined by chiral HPLC. Structures of some representative compounds prepared by this route are shown in FIG. 3.

The inventors have developed a more versatile synthesis strategy where the 2-aminobenzophenone is synthesized on the solid support (Plunkett and Ellman, 1995a). This strategy has been used to construct a library of 11,200 compounds (Bunin et al., 1996). The inventors have also developed a method to employ a silyl linkage where the compound is cleaved from the support by protodesilylation to provide no trace of the solid-phase synthesis sequence (Plunkett and Eliman, 1995b).

C. Library Synthesis

In constructing the libraries the inventors have employed the Chiron Mimotopes pin apparatus, originally developed by Geysen for peptide epitope mapping (Geysen et al., 1987; Valerio et al., 1994). While the libraries synthesized by the inventors to date have been made using the Geysen pin apparatus, the inventors' development of solid-phase synthesis methods has generally been performed on crosslinked aminomethyl polystyrene resin. In this apparatus, 96 polyethylene pins are placed into a supporting block so that each pin fits into a separate well of a 96 well microtiter plate. The pins are pre-derivatized with aminoalkyl groups, providing sites for substrate attachment, and each well of the microtiter plate serves as a distinct reaction vessel for performing chemical reactions. Currently, pin loading levels that range form 100 mol to 50 µmol of material per pin are available. Even 100 nmol of material is sufficient for multiple biological assays, as well as for analytical evaluation of the purity and chemical integrity of the individual compounds.

The inventors initially demonstrated the simultaneous synthesis of 1,4-benzodiazepines on Chiron Mimotopes pin support by the synthesis of a library of 192 compounds that was assembled using all combinations of two 2-aminobenzophenones, twelve amino acids, and eight alkylating agents, with a variety of functionality being displayed (Bunin et al., 1994). This initial benzodiazepine library was synthesized using 100 nmol poly-(acrylic acid) pins. The chemical integrity and yield of many of the compounds in the library were determined by two analytical methods. For 28 of the structurally diverse benzodiazepine derivatives, FAB mass spectrometry confirmed the structure of the compounds corresponding to the major peak (in almost all cases the only peak) observed by HPLC. Yields were also determined for 20 derivatives, where each of the 2-aminobenzophenones, amino acids and alkylating agents was incorporated in at least one of the derivatives. In addition, the spatially separate library of benzodiazepines was screened to obtained detailed structure versus activity information for ligand binding to the cholecystokinin A receptor using a competitive radioligand binding assay.

Figure 4:
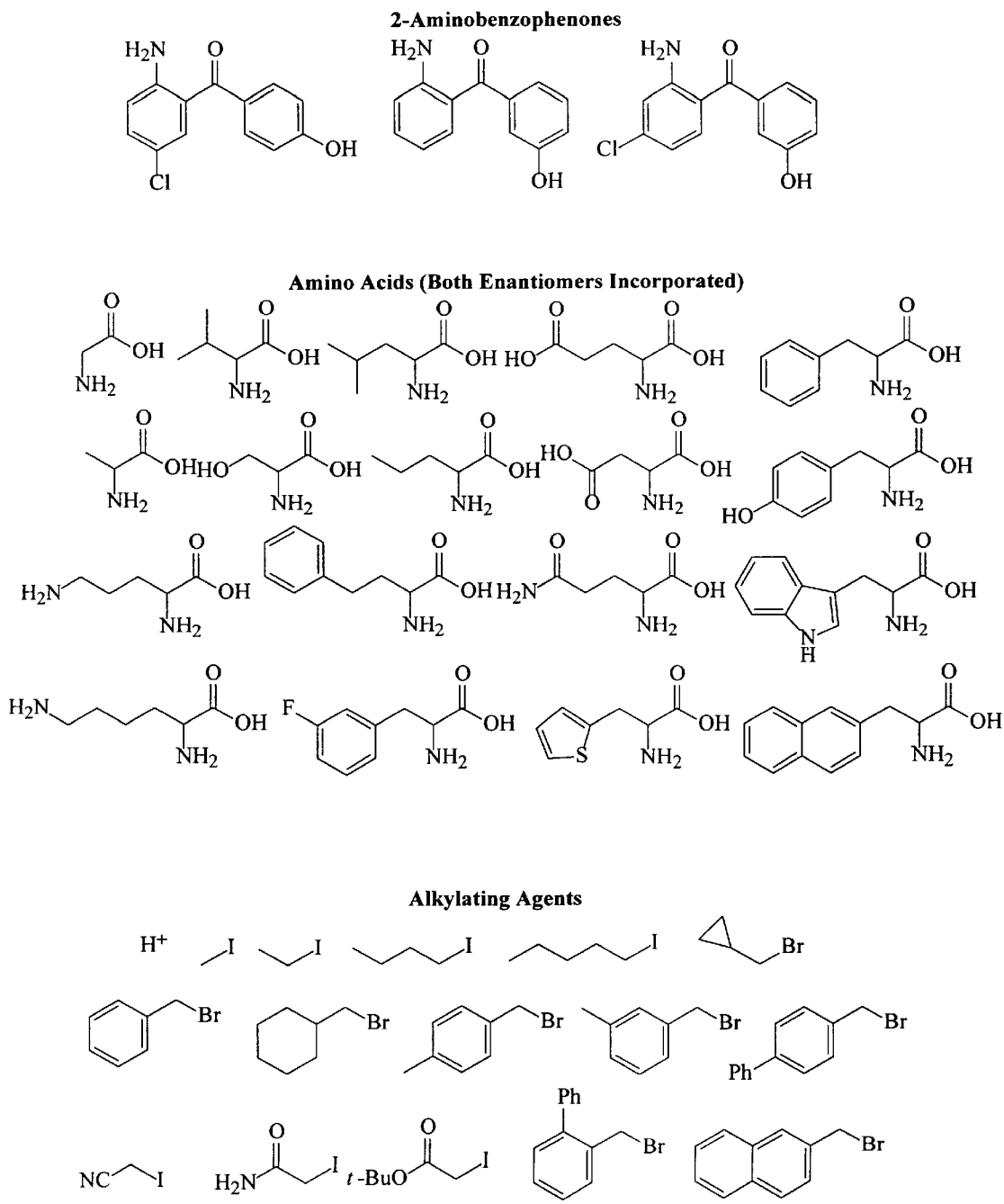
FIG. 4 shows some of the building blocks used in the synthesis of the 1680 compound 1,4-benzodiazepine derivative library.

With the successful synthesis and evaluation of the initial 192 member benzodiazepine library, the methodology was applied to the generation of a larger library for screening against a variety of PTK targets. This second generation library was synthesized from three 2-aminobenzophenones, 35 amino acids, and 16 alkylating agents, providing 1680 1,4-benzodiazepine derivatives (FIG. 4).

The three 2-aminobenzophenones were synthesized in solution, and coupled with the HMP acid labile linker and Fmoc protecting group as previously described (Bunin and Ellman, 1992; Bunin et al., 1994). The 4'-hydroxyl;-5-chloro-2-aminobenzophenone was synthesized by hydrogenation of the corresponding anthranil (Walker, 1962). The 3'-hydroxyl-2-aminobenzophenone and 3'-hydroxyl-4-chloro-2-aminobenzophenone were synthesized using the method of Frye and coworkers (1991). Metal-halogen exchange of 3-bromoanisole (using two equivalents of n-butyllithium) in the presence of the appropriate Weinrib amide, and refluxing of the product in 48% hydrobromic acid, provided the corresponding 2-aminobenzophenone. Both methods provide a straightforward, reliable route to multigram quantities of 2-aminobenzophenones. Natural and unnatural amino acids containing amines, amides, carboxylic acids, alcohols, phenols, thiophenes, and indoles were included. Alkylating agents containing a range of aromatic and aliphatic groups, as well as alkylating agents with hydrogen bond donors and acceptors were incorporated.

The second generation benzodiazepine library was synthesized using the higher loading (1.4 µmol/pin) poly (dimethylacrylamide) pins (Maeji et al., 1994). After removal of the Fmoc protecting group from the amine-derivatized pins, each of the three different Fmoc protected, linker derivatized, aminobenzophenones were quantitatively loaded (as determined by the ninhydrin test) onto the pins in separate flasks employing PyBOP, HOBt, and diisopropylethylamine. Three hundred pins were derivatized with each 2-aminobenzophenone. Two hundred and eighty eight of the pins were used in the synthesis per 2-aminobenzophenone, with the remainder being saved for characterization or replacement. All together eight hundred and sixty four pins (288×3 aminobenzophenones) were used for the synthesis of the library of 1680 benzodiazepine derivatives, since both enantiomers of chiral amino acids were pooled (Glycine was the only achiral amino acid used in the synthesis.).

Once on support the rest of the synthesis sequence proceeded as described for the first generation benzodiazepine library with the exception of the deprotonation/alkylation reaction. The inventors found that in order to achieve good conversion in the alkylation step when using the poly (dimethylacrylamide) pins, it was necessary to add dimethylsulfoxide as a cosolvent during the deprotonation step. In addition, the pins should be sonicated during both the deprotonation and alkylation steps. With these modifications >90% alkylation was generally observed. When working with the lower loading 100 nmol polyacrylic acid pins complete conversion to alkylated product was obtained without the use of sonication or dimethylsulfoxide as cosolvent.

A subset of the library was analyzed by HPLC (as described below in Example 1), and yields were found to range from 61–87% (average 72%). In addition, 48 of the compounds (unpurified, randomly selected, and incorporating each of the building block derivatives at least twice) were analyzed by matrix-assisted laser desorption ionization mass spectrometry (MALDI-MS) using α-cyano-4-hydroxycinnamic acid as the matrix. For 46 of the derivatives the expected molecular ion was found. For one of the undetected derivatives the hydrolytically unstable alkylating agent cyanomethyliodide was used, and the expected unalkylated derivative was found. For the other compound, no product at all was found by HPLC, although good yields were seen for all other library members analyzed that shared at least one building block. This suggests that an aliquotting error lead to loss of the compound.

IV. Analytical Methods

Unless otherwise noted, materials were obtained from commercial suppliers and used without further purification. Fmoc-protected amino acids were purchased from NovaBiochem, and anhydrous N,N-dimethylformamide (DMF) was purchased from Aldrich. Tetrahydrofuran (THF) was distilled from Na/benzophenone, and $CH_2Cl_2$ was distilled from $CaH_2$. The concentration of commercially available solutions of n-butyllithium in hexanes was periodically checked by titration with diphenylacetic acid, as described in Kendall, et al., *J. Org. Chem.*, 1979:44, 1421, incorporated by reference. Organic extracts were dried over $Na_2SO_4$ and concentrated with a rotary evaporator.

Flash chromatography was performed according to the procedure of Still (*J. Org. Chem.*, 1978:43, 2923, incorporated herein by reference) using Merck 60 230–400 mesh silica gel. Reactions and chromatography fractions were analyzed using Analtech 250 μm thin layer chromatography (TLC) plates. Analytical high pressure liquid chromatography was performed on a Rainin HPLC chromatography system employing a 5 μm particle C18 column (4.6 mm×25 cm). Chemical shifts are expressed in ppm relative to internal solvent, and J values are in Hertz. Melting points were determined in open Pyrex capillaries and are uncorrected. Details concerning additional analytical methods are included hereinbelow.

V. Screening Methods

The member compounds of the library were tested against a panel of PTKs for inhibitory activity. The compounds were each screened at a concentration of 100 μM using the assay procedure detailed hereinbelow. Compounds that were inhibitory and showed some selectivity were then picked for scale-up synthesis for validation of their inhibition of PTKs.

VI. Preferred Embodiments

A preferred embodiment of the invention comprises a compound represented by structural formula I,

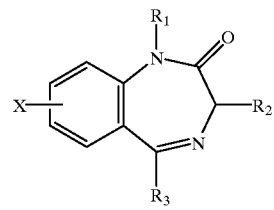

where $R_1$, $R_2$ and $R_3$ are independently described as Y bonded to W, where Y is a 0–6 atom straight or branched saturated or unsaturated chain group comprising C, N, O or S as shown in Table 1, and W is hydrogen or any three membered, four membered, five membered, six membered or fused bicyclic ring system comprising C, N, O or S as shown in Tables 4–9; X is separately and independently selected from Table 2; $R_4$ is hydrogen, alkyl, aryl or acyl; $R_5$ is alkyl or aryl; $R_6$ is hydrogen, alkyl or aryl; and T is independently selected from Table 2; and salts of said compound.

TABLE 1

Description of the Y Spacer Group

where n=0 to 6,

Q may be C, N, O, S, or any combination of these atoms; wherein when Q is O or S, p is 0, and when Q is N or C, p is 0, 1 or 2, and m may be no substituent or any of the following:
H, OH, SH, $NH_2$, halogen, cyano group, nitro, carbonyl oxygen, carboxyl group, sulfonyl group,
k-$CH_3$,
k-$CH_2CH_3$,
k-$CH_2CH_2CH_3$, or
k-$CH(CH_3)_2$ where k=no substituent, O or S

TABLE 2

Ring Substituents for Tables 4–9

X in structural formula I, and $X_1$–$X_8$ in Tables 4–9 may be chosen from:
(1) hydrogen
(2) halogens
(3) alkyl aryl, or acyl
(4) carboxyl, sulfonyl, nitro, or boronyl groups
(5) —O—$R_4$, where $R_4$ is a hydrogen, or an alkyl, aryl, or acyl group
(6) —S—$R_4$, where $R_4$ is a hydrogen, or an alkyl, aryl, or acyl group
(7) —S(O)—$R_5$, where $R_5$ is an alkyl or aryl group
(8) —$SO_2$—$R_5$, where $R_5$ is an alkyl or aryl group
(9) —$SO_2(NR_4)_2$, where $R_4$ is a hydrogen, or an alkyl or aryl group
(10) -cyano group
(11) —$N(R_4)_2$, where $R_4$ is a hydrogen, or an alkyl, aryl, or acyl group or a combination of these
(12) —$N(R_6)_3$, where $R_6$ is a hydrogen, or an alkyl or aryl group

(13) —C(R₄)₂T, where $R_4$ is a hydrogen, or an alkyl, aryl, or acyl group, and T may be chosen from any of the groups described above.

TABLE 3

Nitrogen Substituents for Heterocyclic Rings in Tables 5, 6 and 9

Z in Tables 5, 6, and 9 may be chosen from:
(1) hydrogen
(2) alkyl, aryl, amino, nitro, or halogen groups

TABLE 4

Six-Membered Rings
(X substituents are defined in Table 2)

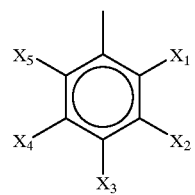
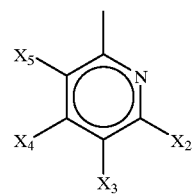
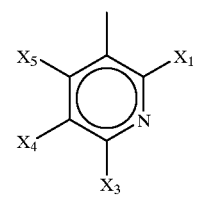
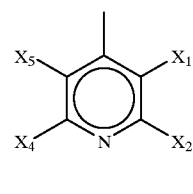
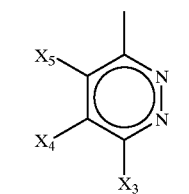
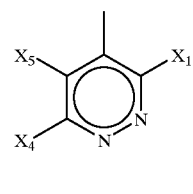
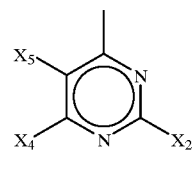
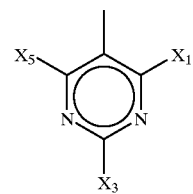
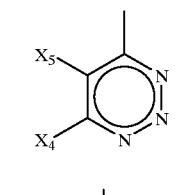
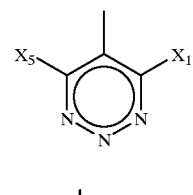
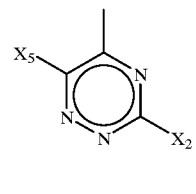
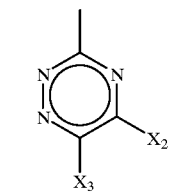

TABLE 4-continued

Six-Membered Rings
(X substituents are defined in Table 2)

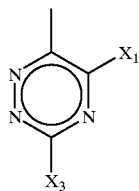
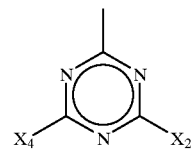

TABLE 5

Azoles and Diazoles
(X substituents are defined in Table 2, and Z substituents are defined in Table 3)

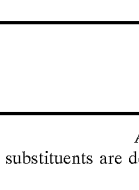
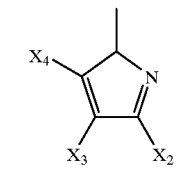
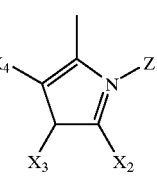
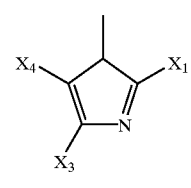
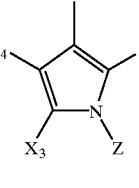
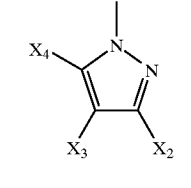
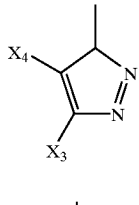
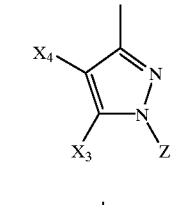
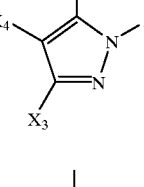
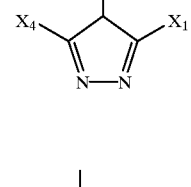

TABLE 5-continued

Azoles and Diazoles
(X substituents are defined in Table 2, and Z substituents are defined in Table 3)

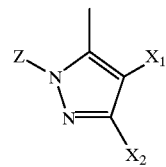 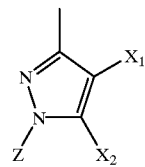

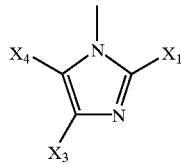 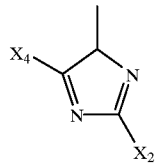

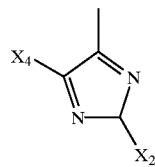 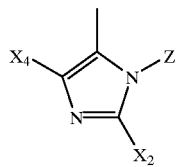

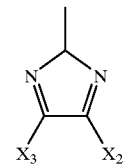 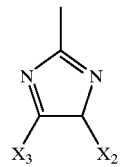

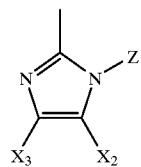 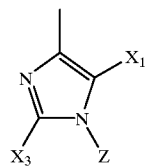

TABLE 6

Triazoles and Tetrazoles
(X substituents are defined in Table 2, and Z substituents are defined in Table 3)

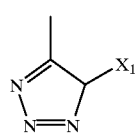 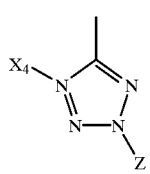

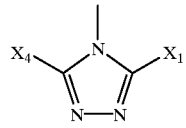 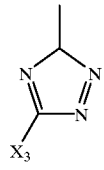
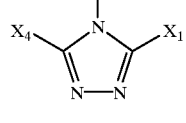 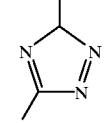

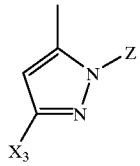 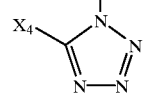

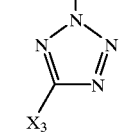 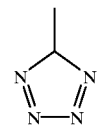

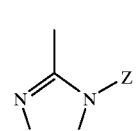 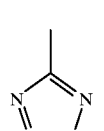
 

TABLE 6-continued

Triazoles and Tetrazoles
(X substituents are defined in Table 2, and Z substituents are defined in Table 3)

TABLE 7

Oxoles and Oxazoles
(X substituents are defined in Table 2)

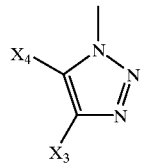 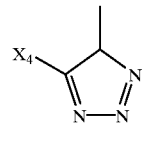 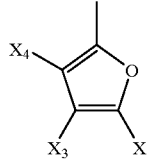 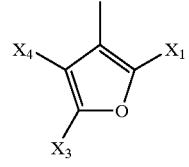

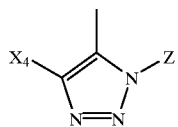 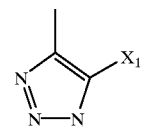 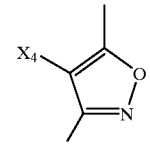 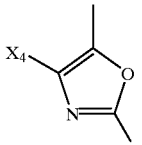

TABLE 7-continued
Oxoles and Oxazoles
(X substituents are defined in Table 2)
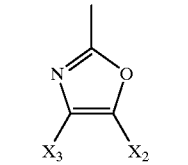
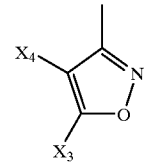
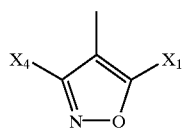
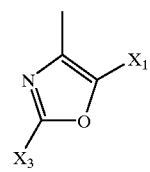
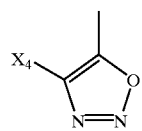
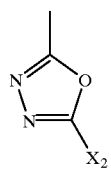
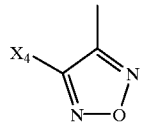
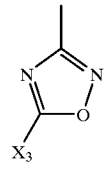
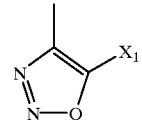
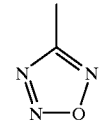
TABLE 8
Thioles and Thiazoles
(X substituents are defined in Table 2)
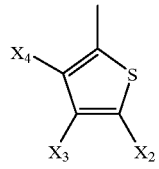
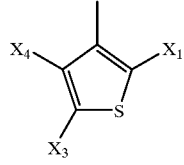
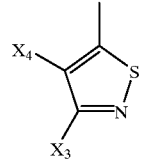
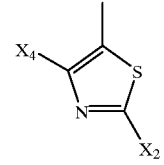
TABLE 8-continued
Thioles and Thiazoles
(X substituents are defined in Table 2)
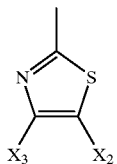
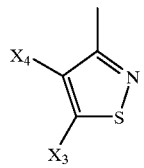
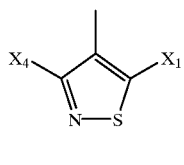
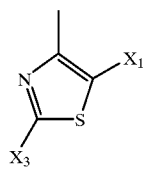
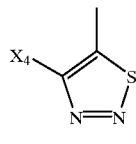
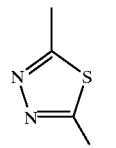
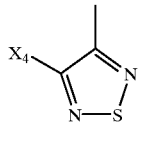
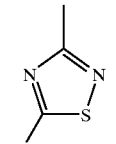
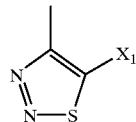
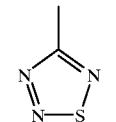
TABLE 9
Cyclic Aliphatic Rings
(D may be carbon, nitrogen, oxygen, or sulfur; X1–X8 are defined in Table 2)
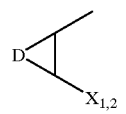
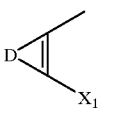
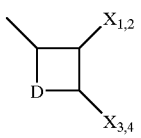
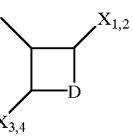
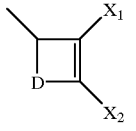
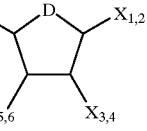

TABLE 9-continued

Cyclic Aliphatic Rings
(D may be carbon, nitrogen, oxygen, or sulfur; X1–X8 are defined in Table 2)

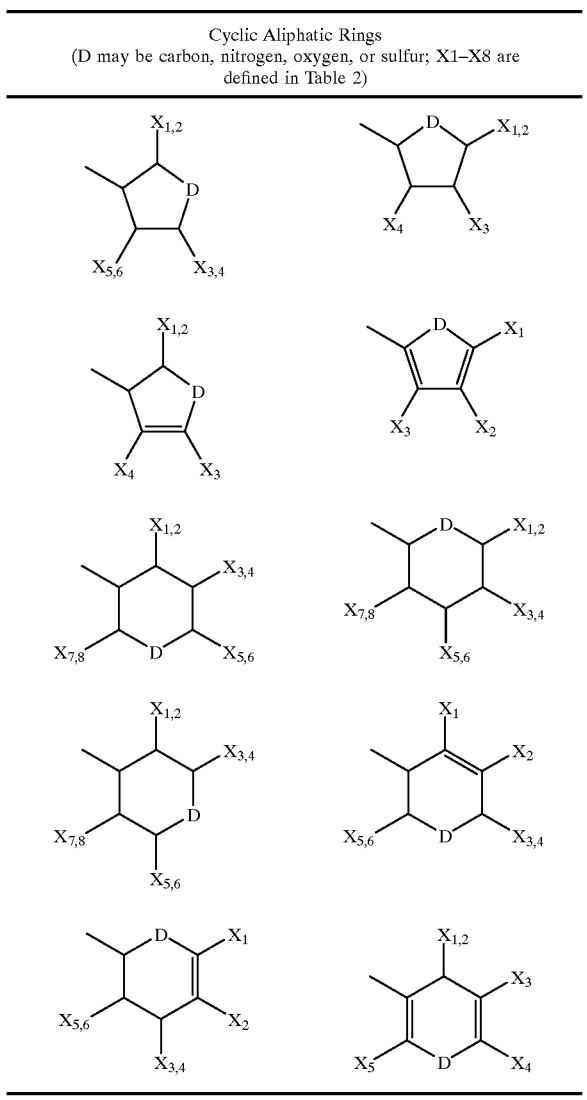

VII. Pharmaceutical Compositions and Routes of Administration

Pharmaceutical compositions of the instant invention comprise an effective amount of one or more of the instant compound(s) dissolved or dispersed in a pharmaceutically acceptable carrier, such as a pharmaceutically acceptable buffer, solvent or diluent, or aqueous medium. Such compositions also can be referred to as inocula.

The phrases "pharmaceutically or pharmacologically acceptable" refer to molecular entities and compositions that do not produce an adverse, allergic or other untoward reaction when administered to a human. As used herein the terms "pharmaceutically acceptable carrier" and "pharmaceutically acceptable buffer, solvent or diluent" include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalents and the like.

As used herein the terms "contact", "contacted" and "contacting", are used to describe the process by which an effective amount of a pharmacological agent, e.g., any of the compounds disclosed in the present invention, comes in direct juxtaposition with the target cell.

For methods of treating mammals, pharmaceutical compositions may be administered by a variety of techniques, such as parenteral, topical or oral administration. For example, the compounds of the instant invention may also be formulated for parenteral administration, e.g., formulated for injection via the intravenous, intramuscular, subcutaneous, or even intraperitoneal routes. The preparation of an aqueous composition that contains one of the inventive compounds as an active ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be employed; and the preparations can also be emulsified.

Solutions of the inventive compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The compounds of the instant invention may also be formulated into a composition in a neutral or salt form. Pharmaceutically acceptable salts include the acid addition salts (formed, e.g., with any free amino groups present), which are formed with inorganic acids such as, for example, hydrochloric or phosphoric acids, or such organic acids as acetic, oxalic, tartaric, mandelic, and the like. Salts formed with any free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compounds of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variations in dosage will necessarily occur depending on the condition of the subject being treated. The person responsible for administration will, in any event, determine the appropriate dose for the individual subject.

VII. Chemotherapeutic Agents

In aspects of the present invention involving cancer treatment, compositions of the present invention can have an effective amount of one or more of the instant PTK inhibitors in combination with an effective amount of a compound (second agent) that is a chemotherapeutic agent as exemplified below. Such compositions will generally be dissolved or dispersed in a pharmaceutically acceptable carrier or aqueous medium.

A wide variety of chemotherapeutic agents may be used in combination with the PTK inhibitors of the present invention. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

1. Antibiotics a. Doxorubicin

Doxorubicin hydrochloride, 5,12-Naphthacenedione, (8s-cis)-10-[(3-amino-2,3,6-trideoxy-α-L-lyxo-hexopyranosyl) oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dl and by 75% if above 3 mg/dl. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

b. Daunorubicin

Daunorubicin hydrochloride, 5,12-Naphthacenedione, (8S-cis)-8-acetyl-10-[(3-amino-2,3,6-trideoxy-α-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DNA-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 10 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

c. Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the d rug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./ml, 1.7 mg./ml, and 0.52 mg./ml, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturate d at relatively low doses, the percent of a dose excreted in urine increases with increasing dose. In children, excretion of intravenously administered mitomycin is similar.

d. Actinomycin D

Actinomycin D (Dactinomycin) [50-76-0]; $C_{62}H_{86}N_{12}O_{16}$ (molecular weight 1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorarnbucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder. The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction.

e. Bleomycin

Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 ml per minute, the serum or plasma terminal elimination half-life of bleomycin is approximately 115 minutes. In patients with a creatinine clearance of <35 ml per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted. Bleomycin may be given by the intramuscular, intravenous, or subcutaneous routes.

2. Miscellaneous Agents a. Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

b. VP16

VP16 is also known as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30 to 60 minute infusion in order to avoid hypotension and bronchospasm, which are probably due to the solvents used in the formulation.

c. Tumor Necrosis Factor

Tumor Necrosis Factor [TNF; Cachectin] is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

3. Plant Alkaloids a. Taxol

Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

b. Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

c. Vinblastine When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes. After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

4. Alkylating Agents a. Carmustine

Carmustine (sterile carmustine) is one of the nitrosoureas used in the treatment of certain neoplastic diseases. It is 1,3 bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$, 40 mg/m$^2$, 50 mg/m$^2$, 60 mg/m$^2$, 70 mg/m$^2$, 80 mg/m$^2$, 90 mg/m$^2$, or 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject b. Melphalan Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma. Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject c. Cyclophosphamide Cyclophosphamide is 2H- 1,3,2-Oxazaphosphorin-2-amine, N,N-bis (2-chloroethyl) tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [$(ClCH_2CH_2)_2$N—$POCl_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day . A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

d. Chlorambucil

Chlorambucil (also known as leukeran) was first synthesized by Everett el al. in 1953. It is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remingtons Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

e. Busulfan

Busulfan (also known as myleran) is a bifunctional alkylating agent. Busulfan is known chemically as 1,4-butanediol dimethanesulfonate. Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

f. Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per ml) and in absolute alcohol (70 mg per ml). Lomustine is relatively insoluble in water (<0.05 mg per ml). It is relatively unionized at a physiological pH. Inactive ingredients in lomustine capsules are magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours. The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these ranges as determined by the clinician to be necessary for the individual being treated.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Benzodiazepine Derivative Library Synthesis

Because of the broad biological activity and desirable pharmacokinetics of 1,4-benzodiazepine derivatives, general and expedient solid-phase synthesis methods for this class of molecules (Bunin and Ellman, 1992; Bunin et al., 1994; DeWitt et al., 1993) as well as the 1,4-benzodiazepine-2,5-dione class (Boojamra et al., 1995; Zuckerman, 1995) have been developed. Using these methods as a starting point, a sub-library of 1680 structurally diverse benzodiazepine derivatives that incorporate a wide variety of chemical functionalities was synthesized.

The sub-library was prepared in a combinatorial fashion beginning with 3 different aminobenzophenones, 15 different alkyl substituents in position R1 and 18 different amino acid side chains in position R2. Outlined below are the preparations of the three aminobenzophenones: 2-amino-5-chloro-4'-hydroxybenzophenone, 3-[3-benzoyl-2-fluorenylmethoxycarbonylaminobenzoyloxymethyl]-phenoxyacetic acid, and 3-[3-benzoyl-5-chloro-2-fluorenylmethoxycarbonylaminobenzoyloxy-methyl]-phenoxyacetic acid, beginning with starting materials and including intermediate compounds. This is followed by a description of the combinatorial synthesis of the 1,4-benzodiazepine derviatives.

Anthranil. α-Nitrobenzaldehyde (15.1 g, 0.100 mol) and phenol 9.46 (0.100 mol) were dissolved in 120 mL of glacial acetic acid in a three-necked round bottom flask. The flask was flushed with $N_2$(g), and the solution was cooled to 0° C. HCl (g) was bubbled through the solution and then through a sodium hydroxide solution to neutralize the acid. The reaction flask was fitted with a rubber stopper and the solution was allowed to warm to ambient temperature and then stirred for 2 h. HCl (g) was removed by bubbling $N_2$ (g) through the solution. The resulting precipitate was filtered and washed with 15 mL of glacial acetic acid to afford 16.2 g (66%) of anthranil. The anthranil was directly reduced to 2-Amino-5-chloro-4'-hydroxybenzophenone (below) without further purification.

2-Amino-5-chloro-4'-hydroxybenzophenone. Anthranil (16.2 g, 65.9 mmol) was dissolved in a mixture of 200 mL of ethyl acetate and 135 mL of ethanol in a parr shaker vessel, and then 1.0 g of 5% palladium on activated carbon was added. The reaction vessel was flushed with $N_2$ (g), and then with $H_2$ (g). The reaction vessel was shaken under $H_2$ (g) at 45 psi in a parr shaker for 4 h. The solution was filtered through Celite to remove the palladium on activated carbon and the solution was concentrated in vacuo. Recrystalization from ethanol/water afforded 14.20 g (88%) of product as light brown crystals: mp 169–171° C. (lit. 173–175° C.). $^1$H NMR (300 MHz, $d_6$-DMSO) δ 6.70 (b, 2), 6.84 (d, 1, J=8.8), 6.78 (d, 2, J=8.6), 7.21 (d, 1, J=2.5), 7.26 (dd, 1, J=2.4, 8.8), 7.50 (d, 2, J=8.6), 10.1 (s, 1); $^{13}$C NMR (75.5 MHz, $d_6$-DMSO) δ 114.3, 116.3, 117.7, 117.8, 128.8, 130.6, 130.9, 132.2, 148.8, 160.3, 194.4. The analytical data was completely consistent with literature values.

Anthranilic acid N-methoxy-N-methylamide. To a solution of N,O-dimethylhydroxylamine hydrochloride (51.2 g, 0.53 mol) in 90% aqueous ethanol (200 mL) was added triethylamine (53 g, 0.53 mol), and, after 10 min stirring at 25° C., isatoic anhydride was added (37.0 g, 0.35 mol) in portions. The reaction was then heated at reflux for 1.5 h and poured onto an equal volume of ice and saturated sodium bicarbonate. The ethanol was then removed by rotary evaporation, the resulting aqueous mixture was extracted with ethyl acetate (3×150 mL), and the combined extracts were washed with water and brine, dried over sodium sulfate and activated charcoal, filtered through celite and concentrated to an orange oil. Flash chromatography with 1:1 diethyl ether/hexanes, and then acetone followed by distillation afforded the product (50.0 g, 79% yield) as a yellow oil. The Weinreb amide (product) was taken directly onto the next step and characterized as 2-amino-3'-hydroxybenzophenone.

2-Amino-3'-methoxybenzophenone. In a flame-dried round bottom flask, anthranilic acid N-methoxyl-N-methylamide (8.00 g, 44.4 mmol) and m-bromoanisidine (8.31 g, 44.4 g) were dissolved in 250 mL of THF and the resulting solution was cooled to −78° C. With vigorous stirring, 2 equiv of nBuLi in hexanes (55.5 mL, 1.6 M, 88.8 mmol) was added dropwise by a syringe pump at 0.6 mL/min. After 20 min, 80 mL of 1 N hydrochloric acid was carefully added, the mixture was extracted with ethyl acetate (600 mL), and the ethyl acetate was washed with water (300 mL) and brine (300 mL), dried over sodium sulfate and concentrated in vacuo. Flash chromatography with 95:5 hexanes/ethyl acetate afforded 6.92 g (69% yield) of 2-amino-3'-methoxybenzophenone as a yellow oil. 2-Amino-3'-methoxybenzophenone was converted to 2-amino-3'-hydroxybenzophenone (below) prior to characterization.

2-Amino-3'-hydroxybenzophenone. 2-Amino-3'-methoxybenzophenone (6.92 g, 30.5 mmol) was dissolved in 125 mL of 48% hydrobromic acid and the solution was heated at refluxed for 12 h. The solvent was removed by rotary evaporation and the resulting red solid was distributed between saturated sodium bicarbonate (400 mL) and $CH_2Cl_2$ (500 mL). The aqueous layer was washed with $CH_2Cl_2$ (2×100 mL) and the combined organic layers were dried with sodium sulfate and concentrated in vacuo to afford 6.03 g (92% yield) of 2-amino-3'-hydroxybenzophenone as a red oil. Recrystalization from ethyl acetate/hexanes (reflux, 4° C.) provided light red crystals: mp 130–132° C., $R_f$ 0.25 (75:25, hexanes/ethyl acetate). $^1$H NMR (500 MHz, $CDCl_3$) δ 5.25 (b, 1), 6.06 (b, 2), 6.58 (dt, 1, J=1.0, 7.5), 6.72 (d, 1, J=8.2), 6.98 (dd, 1, J=2.2, 8.2), 7.07 (t, 1, J=2.0), 7.15 (d, 1, J=7.5), 7.28 (m, 2), 7.45 (dd, 1, J=1.5, 8.0). $^{13}$C NMR (101 MHz): δ 77.2, 115.6, 115.7, 117.0, 118.2, 121.7, 129.4, 134.4, 134.6, 141.6, 150.9, 155.4. HRMS (FAB, m-nitrobenzyl alcohol) calcd for $C_{13}H_{11}NO_2$ (M+H) 214.0843, found 214.0867.

4-(2-Amino-3-benzoylphenoxymethyl)phenoxyacetic acid allyl ester. 2-Amino-3'-hydroxybenzophenone (4.82 g, 22.4 mmol) was dissolved in 70 mL of N,N-dimethylformamide (DMF). Potassium bis(trimethylsilyl) amide that was 0.5 M in toluene (44.9 mL, 22.4 mmol, 1.0 equiv) was added dropwise with stirring. Allyl 2-(4-bromomethylphenoxy)acetate (5.97 g, 20.8 mmol, 0.95 equiv) was added and the resulting brown slurry was stirred at ambient temperature for 45 min. The slurry was concentrated in vacuo, diluted with $CH_2Cl_2$ (150 mL) and extracted with 1 N aqueous sodium bicarbonate (3×100 mL) and with 1 N aqueous sodium chloride (100 mL), and then concentrated to give a yellow solid (8.96 g, 100%, unpurified yield). The unpurified product was predominately one spot by TLC without chromatography and thus was taken directly on to the next step and fully characterized as 3-[3-Benzoyl-2-fluorenylmethoxycarbonylaminobenzoyloxymethyl]-phenoxyacetic acid. 4-(2-Amino-3-benzoylphenoxymethyl) phenoxyacetic acid allyl ester: $R_f$ (50:50 ethyl acetate/hexane).

4-(3-Benzoyl-2-fluorenylmethoxycarbonylamino-phenoxymethyl) phenoxyacetic acid allyl ester. 4-(2-Amino-3-benzoylphenoxymethyl)-phenoxyacetic acid allyl ester (9.03 g, 20.8 mmol) and freshly distilled pyridine (1.97 g, 25.0 mmol, 1.2 equiv) were dissolved in 100 mL of $CH_2Cl_2$. The resulting yellow solution was cooled to 0° C., and fluorenylmethoxycarbonyl chloride (4.83 g, 21.8 mmol, 1.05 equiv) was added. The resulting solution was stirred at 0° C. for 15 min and then at ambient temperature for 1 h. The solution was diluted with CH$_2$Cl$_2$ (150 mL), extracted twice with 1 N aqueous sodium bisulfate (100 mL), once with dilute aqueous sodium chloride (100 mL), and then concentrated to give a yellow foam. Silica gel chromatography with CH$_2$Cl$_2$ afforded 8.68 g (65% yield) of purified material as a white solid that was homogeneous by $^1$H NMR. The carboxylic acid (3-[3-Benzoyl-2-fluorenylmethoxycarbonylaminobenzoyloxymethyl]-phenoxyacetic acid) was full characterized after removal of the allyl ester.

3-[3-Benzoyl-2-fluorenylmethoxycarbonylaminobenzoyloxymethyl]-phenoxyacetic acid. 3-[3-benzoyl-2-fluorenylmethoxycarbonylamino-benzoyloxymethyl]-phenoxyacetic acid allyl ester (8.68 g, 14.3 mmol) was dissolved in 150 mL of CH$_2$Cl$_2$. Tetrakis(triphenylphosphine)palladium (331 mg, 0.286 mmol, 0.02 equiv) was added, and after flushing the reaction flask with N$_2$, tributyltin hydride (4.23 g, 15.7 mmol, 1.1 equiv) was added slowly dropwise with stirring over 3 minutes. The reaction solution turned from bright yellow to brown over 45 minutes. The reaction solution was then diluted with CH$_2$Cl$_2$ (150 mL) and was extracted three times with 0.5 N aqueous hydrochloric acid (100 mL) once with aqueous sodium chloride (100 mL), then dried over sodium sulfate amid concentrated in vacuo. Flash chromatography with 50:50:1 ethyl acetate/hexanes/acetic acid followed by toluene azeotrope afforded an off-white solid which was recrystallized from CH$_2$Cl$_2$ and hexanes to provide the pure product as an off-white solid (5.10 g, 59% yield): mp 130–131° C., R$_f$ 0.50 (98:2, ethyl acetate/acetic acid). $^1$H NMR (500 MHz, CDCl$_3$); δ 4.29 (t, 2, J=7.4), 4.44 (d, 2, J=7.3), 4.68 (s, 2), 5.04 (s, 2) 6.93 (d, 2, J=7.3), 7.03 (t, 1, J=7.5), 7.25 (m, 10), 7.56 (t, 2, J=7.4), 7.65 (d, 2, J=7.4), 7.76 (d, 2, J=7.5), 8.39 (d, 1, J=7.8), 10.4 (s, 1). $^{13}$C NMR (101 MHz): δ 46.9, 64.7, 67.4, 69.7, 114.8, 115.3, 119.5, 119.9, 120.0, 121.3, 122.6, 125.1, 127.1, 127.6, 129.2, 129.3, 130.0, 133.6, 134.2, 129.9, 140.7, 141.2, 143.7, 153.7, 158.5, 199.0. Anal. Calcd for C$_{37}$H$_{29}$NO$_7$: C, 74.1; H, 4.87; N, 2.34. Found: C, 74.13; H, 4.86; N, 2.08.

4-Chloroanthranilic acid N-methoxy-N-methylamide. To a solution of N,O-dimethylhydroxylamine hydrochloride (7.24 g, 74.2 mmol) in 90% aqueous ethanol (30 mL) was added triethylamine (7.42 g, 74.2 mmol), and, after 10 min stirring at 25° C., 4-chloroisatoic anhydride was added (9.71 g, 49.0 mmol) in portions. The reaction was then heated at reflux for 1.5 h and poured onto an equal volume of ice and saturated sodium bicarbonate. The ethanol was then removed by rotary evaporation, the resulting aqueous mixture was extracted with ethyl acetate (3×150 mL), and the combined extracts were washed with water and brine, dried over sodium sulfate and activated charcoal filtered through celite and concentrated to an orange oil. Flash chromatography with 1:1 diethyl ether/hexanes, and then acetone followed by distillation afforded 20b (4.58 g, 29% yield) as a yellow oil. R$_f$ 0.20 (9:1, hexanes/ethyl acetate). $^1$H NMR (300 MHz, CDCl$_3$); δ 3.33 (s, 3), 3.56 (s, 3), 6.64 (dd, 1, J=1.0, 8.3), 6.69 (d, 1, J=1.0), 7.34 (d, 1, J=8.3). The Weinreb amide (product) was taken directly onto the next step and fully characterized as 2-amino-4-chloro-3'-hydroxybenzophenone.

2-Amino-4-chloro-3'-methoxybenzophenone. In a flame-dried round bottom flask 4-chloroanthranilic acid N-methoxy-N-methylamide (4.58 g, 21.3 mmol) and m-bromoanisidine (4.02 g, 21.5 g) were dissolved in THF (185 mL) and the resulting solution was cooled to −78° C. With vigorous stirring, 2 equiv of nBuLi in hexanes (26.9 mL, 1.6 M, 43.0 mmol) was added dropwise by a syringe pump at 0.6 mL/min. After 20 min, 40 mL of 1 N hydrochloric acid was carefully added, the mixture was extracted with ethyl acetate (300 mL), and the ethyl acetate was washed with water (100 mL) and brine (100 mL), dried over sodium sulfate and concentrated in vacuo. Flash chromatography with hexanes/ethyl acetate (95:5, then 75:25) afforded 3.75 g (67% yield) of 2-amino-3'-methoxybenzophenone as a yellow oil. $^1$H NMR (50 MHz, CDCl$_3$): δ 3.83 (s, 3), 6.17 (b, 2), 6.55 (dd, 1, J=2.0, 8.5), 6.72 (d, 1, J=2.0), 7.06 (dd, 1, J=2.6, 8.5), 7.13 (m, 2), 7.35 (t, 1, J=7.8), 7.39 (d, 1, J=8.5). 2-Amino-4-chloro-3'-methoxybenzophenone was converted to 2-amino-4-chloro-3'-hydroxybenzophenone (below) prior to full characterization.

2-Amino-4-chloro-3'-hydroxybenzophenone. 2-Amino-4-chloro-3'-methoxybenzophenone (3.75 g, 14.3 mmol) was dissolved in 90 mL of 48% hydrobromic acid and the solution was heated at refluxed for 12 h. The solvent was removed by rotary evaporation and the resulting red solid was distributed between saturated sodium bicarbonate (200 mL) and CH$_2$Cl$_2$ (250 mL). The aqueous layer was washed with CH$_2$Cl$_2$ (2×100 mL) and the combined organic layers were dried with sodium sulfate, filtered through celite and concentrated in vacuo to afford 2.95 g (83% yield) of 2-amino-4-chloro-3'-hydroxybenzophenone (22b) as a yellow solid: mp 137–138° C., R$_f$ 0.15 (75:25, hexanes/ethyl acetate). $^1$H NMR (500 MHz, CDCl$_3$); δ 6.16 (b, 2), 6.55 (dd, 1, J=2.0, 8.5), 6.72 (d, 1, J=1.9), 6.99 (dd, 1, J=2.5, 8.1), 7.05 (t, J=2.0), 7.12 (d, 1, J=7.8), 7.30 (t, 1, 7.8), 7.38 (d, 1, J=8.6). $^{13}$C NMR (101 MHz): δ 115.6, 116.1, 116.2, 118.4, 120.3, 121.6, 126.1, 129.5, 135.9, 142.2, 154.3. HRMS (FAB, m-nitrobenzyl alcohol) calcd for C$_{13}$H$_{10}$ClNO$_2$ (M+H) 248.0046, found 248.0484.

4-(2-Amino-4-chloro-3-benzoylphenoxymethyl) phenoxyacetic acid allyl ester. 2-Amino-4-chloro-3'-hydroxybenzophenone (2.95 g, 11.9 mmol) was dissolved in 35 mL of N,N-dimethylformamide (DMF). Potassium bis(trimethylsilyl)amide that was 0.5 M in toluene (23.8 mL, 11.9 mmol, 1.0 equiv) was added dropwise with stirring. Allyl 2-(4-bromomethyl-phenoxy)acetate (3.23 g, 11.3 mmol, 0.95 equiv) was added and the resulting brown slurry was stirred at ambient temperature for 45 min. The slurry was concentrated in vacuo, diluted with CH$_2$Cl$_2$ (75 mL) and extracted with 1 N aqueous sodium bicarbonate (3×100 mL) and with 1 N aqueous sodium chloride (100 mL), and then concentrated to give a yellow solid. Chromatography with petroleum ether/ethyl acetate (70:30) afforded 2.40 g (45% yield) of 4-(2-amino-4-chloro-3-benzoylphenoxymethyl)-phenoxyacetic acid allyl ester: R$_f$ 0.2 (50:50 ethyl acetate/hexane). 4-(2-amino-4-chloro-3-benzoylphenoxymethyl)phenoxyacetic acid allyl ester was taken directly on to the next step and fully characterized as 23b.

4-(3-Benzoyl-2-fluorenylmethoxycarbonylamino-phenoxymethyl) phenoxyacetic acid allyl ester. 4-(2-Amino-3-benzoylphenoxymethyl)-phenoxyacetic acid allyl ester (2.40 g, 5.30 mmol) and freshly distilled pyridine (0.50 mL, 6.36 mmol, 1.2 equiv) were dissolved in 30 mL of CH$_2$Cl$_2$. The resulting yellow solution was cooled to 0° C., and fluorenylmethoxycarbonyl chloride (1.44 g, 5.56 mmol, 1.05 equiv) was added. The resulting solution was stirred at 0° C. for 15 min and then at ambient temperature for 1 h. The solution was diluted with CH$_2$Cl$_2$ (200 mL), extracted twice with 1 N aqueous sodium bisulfate (100 mL), once with dilute aqueous sodium chloride (100 mL), and then concentrated to give a yellow foam. Recrystallization from $CH_2Cl_2$/hexanes (reflux to 20° C.) afforded 3.41 g (95% yield) of purified material as a yellow solid that was homogeneous by $^1H$ NMR. The carboxylic acid (3-[3-Benzoyl-5-chloro-2-fluorenylmethoxycarbonylaminobenzoyloxy-methyl]-phenoxyacetic acid) was fully characterized after removal of the allyl ester.

3-[3-Benzoyl-5-chloro-2-fluorenylmethoxycarbonylaminobenzoyloxy-methyl]-phenoxyacetic acid. 4-[4-benzoyl-5-chloro-2-fluorenyl-methoxycarbonylaminobenzoyloxymethyl]-phenoxyacetic acid allyl ester (3.41 g, 5.05 mmol) was dissolved in 50 mL of $CH_2Cl_2$. Tetrakis(triphenyl-phosphine)palladium (123 rag, 0.100 mmol, 0.02 equiv) was added, and after flushing the reaction flask with $N_2$, tributyltin hydride (1.62 g, 5.55 mmol, 1.1 equiv) was added slowly dropwise with stirring over 3 minutes. The reaction solution turned from bright yellow to brown over 45 minutes. The reaction solution was then diluted with $CH_2Cl_2$ (150 mL) and was extracted three times with 0.5 N aqueous hydrochloric acid (100 mL) once with aqueous sodium chloride (100 mL), then dried over sodium sulfate. Flash chromatography with 50:50:1 ethyl acetate/hexanes/acetic acid followed by toluene azeotrope afforded a yellow solid which was recrystallized from $CH_2Cl_2$ and hexanes to provide the pure product as a yellow solid (2.71 g, 81% yield): mp 139–140° C., $R_f$ 0.53 (98:2, ethyl acetate/acetic acid). $^1H$ NMR (500 MHz, $CDCl_3$): δ 4.29 (t, 2, J=7.4), 4.45 (d, 2, J=7.4), 4.68 (s, 2), 5.04 (s, 2), 6.93 (d, 2, J=8.5), 6.98 (d,2, J=8.5), 7.19 (d, 1,J=8.4), 7.30 (m, 8), 7.48 (d, 1,J=8.5), 7.65 (d, 2,J=7.4), 7.76 (d, 2, J=7.5), 8.52 (s, 1), 10.6 (s, 1). $^{13}C$ NMR (101 MHz): δ 14.0, 22.5, 46.9, 64.8, 67.6, 69.7, 114.8, 115.2, 119.6, 119.8, 119.9, 120.6, 121.5, 122.3, 125.1,127.1, 127.7, 129.2, 129.4, 129.9, 134.7, 139.7, 140.8, 141.2, 142.0, 143.5, 153.3, 157.3, 158.5, 198.3. HRMS (FAB, m-nitrobenzyl alcohol) calcd for $C_{37}H_{28}ClNO_7$ (M+H) 633.1620, found 633.1632.

Fmoc-protected amine-derivatized pins are supplied by Chiron Mimotopes (Victoria, Australia). Fmoc-protected amino acids (including side-chain preprotected derivatives; Bunin et al., 1994) and 4-hydroxymethylphenoxyacetic acid were purchased from Nova Biochem (San Diego, Calif.) or Bachem Bioscience Inc. (King of Prussia, Pa.). All other reagents and solvents were purchased form Aldrich (Milwaukee, Wis.). When measuring out pins, a useful alternative to counting large numbers is determining the average weight of one pin. In working with sets of pins that are not in a pin block, a peptide flask (SafeLab, catalog number M270) is often useful for filtration and rinsing operations. (A peptide flask is a glass cylinder with a fine frit at the bottom and a three-way valve beneath the frit. Solvents may be forced through by nitrogen pressure at the top, and reaction mixtures may be gently agitated by bubbling in nitrogen from the bottom.) Chemical synthesis was performed in chemically resistant polypropylene deep well microtiter plates purchased from Beckman (Fullerton, Calif.), catalog #267006. When working with sets of pin blocks, the polypropylene lids from micropipette tip boxes are convenient, chemically stable reservoirs for rinses and deprotection reactions. A set of printed documentation for the library synthesis was prepared in advance. This is used as a checklist during the construction of the library, and is a very important part of the overall process.

The Fmoc-protected amines on 1.4 μmol pins (Chiron Mimotopes Ltd.) were deprotected with 20% piperidine in DMF for 20 min. The pins were then rinsed four times with DMF and four times with methanol and dried under vacuum. For each of the three 2-aminobenzophenones incorporated in to the library, 288 pins (18 amino acids times 16 alkylating agents) were needed. Deprotected pins (300, 0.42 mmol) were added to a round bottom flask containing DMF (56 mL), phenoxyacetic acid 1 (2.8 mmol, 7 equiv), see FIG. 1, 1-hydroxybenzotriazole (2.8 mmol, 7 equiv), PyBOP (2.8 mmol, 7 equiv), and diisopropylethylamine (4.2 mmol, 10.5 equiv). The acylation was allowed to proceed for 12 h. The pins were rinsed with DMF (3×), methanol (3×), and air dried. The Fmoc protecting group of the 2-aminobenzophenones 2 was removed by treatment of the pins with 20% piperidine in DMF (1 min, then 20 min), see FIG. 2. The pins were rinsed with DMF, methanol (3×), and air dried. The derivatized pins were placed into the pin blocks and all subsequent steps were performed in deep-well microtiter plates.

The amino acid Fmoc protecting group was removed by treatment of the pin blocks with 20% piperidine in DMF for 20 min. The pin blocks were rinsed with DMF, MeOH (3×), and air dried. The pin blocks were immersed in 5% acetic acid in DMF or NMP at 65° C. in a thermostated oven for 12 h to provide the cyclic product 4, see FIG. 2. The pins were rinsed with DMF (2×), MeOH (2×), THF (2×), and air-dried. After THF and DMSO rinses, the pin blocks were immersed in a 1:1 (v/v) solution of 0.12 M solution of lithiated 5-phenylmethyl-2-oxazolidinone in 10% DMF in THF/DMSO and sonicated for one hour. For the sonication, the pin blocks were placed in plastic ziplock bags to maintain dryness (although the inventors have found that 2% water does not adversely affect the alkylation step). The pin blocks were removed from the bags and were then immersed, without rinsing, in a 0.40 M solution of alkylating agent in DMF (prepared immediately before alkylation) and sonicated for an additional three hours (again in a ziploc bag), to provide the fully functionalized, support-bound derivatives 5, see FIG. 2. The pin blocks are removed from the ziplock bag and rinsed with DMF, DMF/$H_2O$, MeOH (air dried), and $CH_2Cl_2$.

Figure 2:
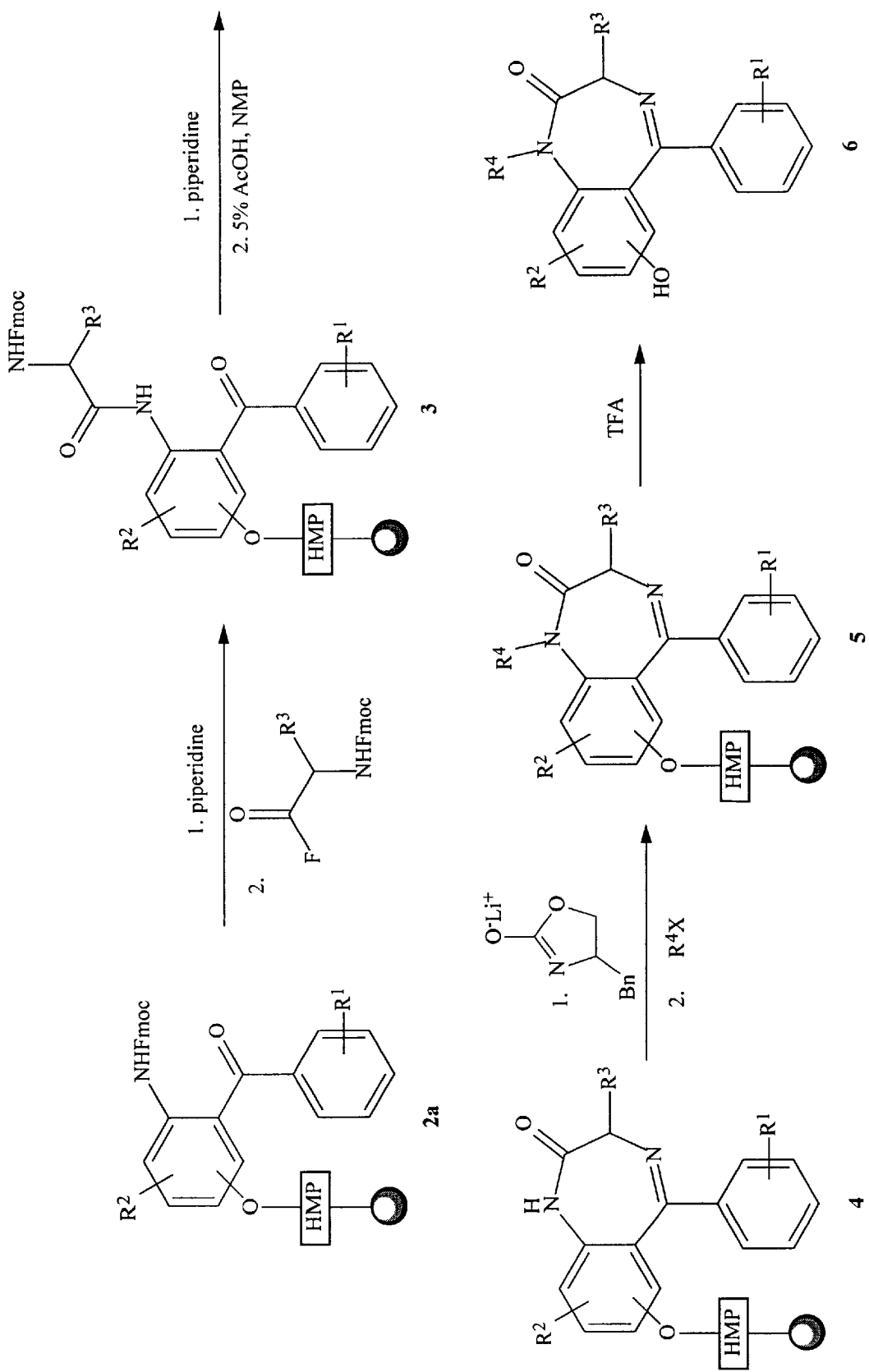
FIG. 2 shows schematically the solid phase synthesis of 1,4-benzodiazepines.

The derivatives 5 are cleaved from the support by placing the pin blocks into microtiter plates that contain 0.25 mL/well of a solution of 85:10:5 trifluoroacetic acid/$Me_2S$/$H_2O$ for 24 h, see FIG. 2. For benzodiazepine derivatives incorporating tryptophan, 85:5:5:5 trifluoroacetic acid/dimethylsulfide/$H_2O$/1,2-ethanedithiol is employed as the cleavage cocktail to prevent oxidative decomposition of the indole ring (Fields and Noble, 1990). The cleavage cocktail is then removed with a Jouan RC10.10 concentrator equipped with a microtiter-plate rotor to provide the free 1,4-benzodiazepine derivatives 6, spatially separated in the individual wells of the microtiter plate (FIG. 2).

Evaluation of the 1,4-benzodiazepine derivatives is accomplished by reverse phase HPLC analysis using a Rainin $C_{18}$ column and a gradient (over 40 min) of 15% to 100% methanol in water buffered with 0.1% trifluoroacetic acid with UV detection at 350 nm. The compound corresponding to the major peak (usually the only peak) can be isolated and submitted for mass spectrometric analysis to verify the structure of the benzodiazepine derivative. Exact yields for synthesis on pin supports can be determined by addition of a stock solution of fluorenone in DMF followed by reverse-phase HPLC analysis to determine the relative peak area of the 1,4-benzodiazepine derivative to the fluorenone standard. The quantity of material produced per pin can then be calculated from the extinction coefficients of the derivatives that are determined on material prepared on large scale. Alternately, yields can be determined by addition of an aliquot of p-xylene as an internal proton NMR standard followed by peak area integration. Characterization of the unpurified benzodiazepine products may be performed by matrix-assisted laser desorption ionization mass spectrometry (MALDI-MS) using α-cyano-4-hydroxycinnamic acid as matrix.

EXAMPLE 2

Screening for Candidate Compounds

With the second generation 1,4-benzodiazepine library from Example 1 above, the inventors have identified inhibitors of $pp60^{c-src}$ Budde et al., 1995. Active compounds from the library were synthesized on large scale, purified by chromatography, and fully characterized to allow exact determination of $IC_{50}$ values. Recently, multigram quantities of the most active 1,4-benzodiazepines have been synthesized on solid support for in vivo testing; The compounds were synthesized on solid supports because this provides the fastest, least expensive route for the syn thesis of moderate amounts of the compounds.

The sub-library consisted of 1,680 compounds with 15 different alkyl substituents in position R1 and 18 different amino acid side chains in position R2. From screening this library the inventors obtained 18 "hits" against Src EGFr and Csk. Nine compounds had selectivity for Src and these were further analyzed by a rough $IC_{50}$ value which validated five compounds (R1 was a benzyl or phenyl-benzyl group, and R2 was a tyrosine or napthalalanine) for further study. The three best compounds (FIG. 5, FIG. 6, and FIG. 7) were synthesized in milligram quantity (Example 3 below) and further analyzed for in vitro selectivity (Example 4 below).

The compounds within the library were screened at a concentration of 100 μM using the following assay procedure. A 10 μL aliquot of poly(Glu:Tyr, 4:1) to final concentration of 200 μg/mL, 20 μL of benzodiazepine to be tested, 10 μL of purified Src and 10 μL of [gamma-$^{32}$P]-ATP-MgCl$_2$ cocktail (final concentration of 0.2 mM ATP; specific activity of 600 dpm/pmol, and 6 mM MgCl$_2$) were mixed and incubated in 0.5 mL test tubes at ambient temperature. After 30 min, a 35 μL aliquot was spotted onto a 1×1 inch 3 MM filter paper and dropped into a 5% TCA bath at 60° C. The filter papers were washed 3 times with 5% TCA and air dried. The filter papers were then placed into a vial, 3 mL scintillation cocktail added, and analyzed by liquid scintillation counting. Compounds that were inhibitory and showed some selectivity were then picked for scale-up synthesis for validation of their inhibition of Src.

EXAMPLE 3

Synthesis of 7-chloro-1,3-dihydro-1-(-4-biphenylmethyl)-3-(-4-hydroxyphenylmethyl)-5-(4-hydroxyphenyl)-(2H)1,4-benzodiazepin-2-one The following example describes the milligram-scale synthesis on solid support of a preferred compound of the present invention, 7-chloro-1,3-dihydro-1-(-4-biphenylmethyl)-3-(-4-hydroxyphenylmethyl)-5-(4-hydroxyphenyl)-(2H) 1,4-benzodiazepin-2-one.

From 208 mg (0.100 mmol) of aminomethylpolystyrene (2% divinylbenzene) (0.480 mmol/g support) was obtained 34 mg (61% yield) of product after purification on 2×15 cm silica gel with 25:75:1 then 50:50:1 ethyl acetate/hexane/acetic acid as the eluent. $R_f$ 0.38 (50:50:1, ethyl acetate/hexane/acetic acid). $^1$H NMR (300 MHz, 16% CD$_3$OD in CDCl$_3$): δ 3.30 (dd, 1, J=7.5, 13.9), 3.45 (dd, 1 J=6.2, 13.9), 3.68 (t, 1, J=6.2), 4.67 (d, 1, J=15.3), 5.58 (d, 1, J=15.3), 6.61 (d, 2, J=8.5), 6.62 (d, 2, J=9.7), 6,89 (d, 2, J=8.2), 6.98 (m, 4), 7.27 (m, 10). $^{13}$C NMR (101 MHz): δ 36–3, 49.6, 64.9, 80.2, 114.7, 114.8, 122.4, 122.8, 123.2, 123.9, 126.5, 127.0. 127.5, 128.4, 128.9, 129.4, 129.6, 129.8, 130.4, 131.1, 131.2, 132.1, 135.0, 139.7, 140.1, 154.9, 159.4, 169.4. LRMS (FAB, thioglycerol/glycerol) calcd for $C_{35}H_{27}ClN_2O_3$ (M+1) 559, found 559.

EXAMPLE 4

Comparison of Instant Inhibitors to Peptide Based Inhibitors

It is difficult to make a direct comparison of the affinity of the instant benzodiazepine inhibitors versus other PTK inhibitors since most are not commercially available. However, the inventors compared the benzodiazepines with the published peptide inhibitors of Src. The benzodiazepines are more potent inhibitors than most of the published peptides. The peptides have less than 10-fold selectivity for Src. Furthermore, peptides are inherently poor drug candidates due to their polar nature and amide bonds which are susceptible to hydrolysis.

TABLE 10

Comparison of Peptides and Benzodiazepines as Inhibitors of Src

| Number | Identification | Ki (μM) | Reference |
|---|---|---|---|
| 1 | L-Tyr,BnzPh(see FIG. 5) | 20 | Present Invention |
| 2 | D-Tyr,BnzPh(see FIG. 6) | 43 | Present Invention |
| 3 | L-Tyr,Bnz(see FIG. 7) | 74 | Present Invention |
| 4 | DRVYVHPF | 3,100 | Wong and Goldberg, 1983 |
| 5 | RDRVYVHPF | 2,600 | Wong and Goldberg, 1983 |
| 6 | RRLIEDAEYAARG | 10,000 | Casnellie et al., 1982 |
| 7 | KVEKIGBGTYGRVYK | 400 | Litwin et al., 1991 |
| 8 | (YGE)$_5$YGD | 33 | Budde et al., 1995 |
| 9 | EFEYAFF | 130 | Ramdas et al., 1995 |
| 10 | YIYGSFK | 1,600 | Lam et al., 1995 |
| 11 | EEIYGEFE | 70 | Songyang et al., 1995 |
| 12 | KKSRGDYMTMQIG | 200 | Garcia et al., 1993 |

EXAMPLE 5

Differential Inhibition Assays

Recombinant Src was expressed using the baculovirus-insect cell system and purified as published (Budde et al, 1993). Recombinant Csk, Lck, Abl, and the FGFr were expressed as glutathione-S-transferase fusion proteins using the pGEX expression vector and *E. coli*, and purified as described (Sun and Budde, 1995).

The tyrosine kinase activity of Src, Lck (p56$^{lck}$), Csk (C-Src kinase), Abl (Bcr-Abl catalytic domain), and the FGFr (fibroblast growth factor receptor catalytic domain), was determined using poly E$_4$Y and $^{32}$P-ATP. Briefly, enzymes were assayed in a reaction mixture consisting of 0.15 M EPPS-NaOH (pH 8.0) with 6 mM MgCl$_2$, 0.2 mM $^{32}$P-ATP (0.2–0.4 mCi/μmol), 10% glycerol, 0.1% Triton X-100, and poly E$_4$Y. For screening assays, 50 μg/mL poly E$_4$Y was used, and for Ki determinations variable concentrations (0, 20, 30, 75, and 150 μg/mL) of poly E$_4$Y were used.

As mentioned above, to reduce potential toxicity, inhibitors have been developed that can selectively inhibit Src. The three "lead compounds" shown in FIG. 5, FIG. 6, and FIG. 7 were tested against a panel of other PTKs, protein kinase A (PKA), which is a Ser/Thr kinase, the ATP utilizing enzymes hexokinase (HXK), and lactate dehydrogenase (LDH) (Table 11). The benzodiazepine with the best affinity and selectivity (L-Tyr,BnzPh, see FIG. 5) was further examined for its mode of inhibition and Ki values against the enzyme panel (data shown in Table 12). L-Tyr,BnzPh was a "mixed" type of inhibitor (i.e., it affected both the Km and Vmax value) against either variable ATP or variable poly $E_4Y$. Analysis of inhibition by mixtures of inhibitors to determine if the benzodiazepines were binding at the active site could not be performed since the solvent for solubilizing the benzodiazepines interfered with the inhibition by alternative peptide substrates acting as inhibitors. However, using a series of Csk deletion mutants the binding site was determined to be the catalytic domain (SH1 domain). Catalytically active mutants devoid of the SH2 or SH3 domain were found to equally inhibit the kinase activity of Csk, suggesting that they bind to the SH 1 or catalytic domain.

TABLE 11

Figure 5:
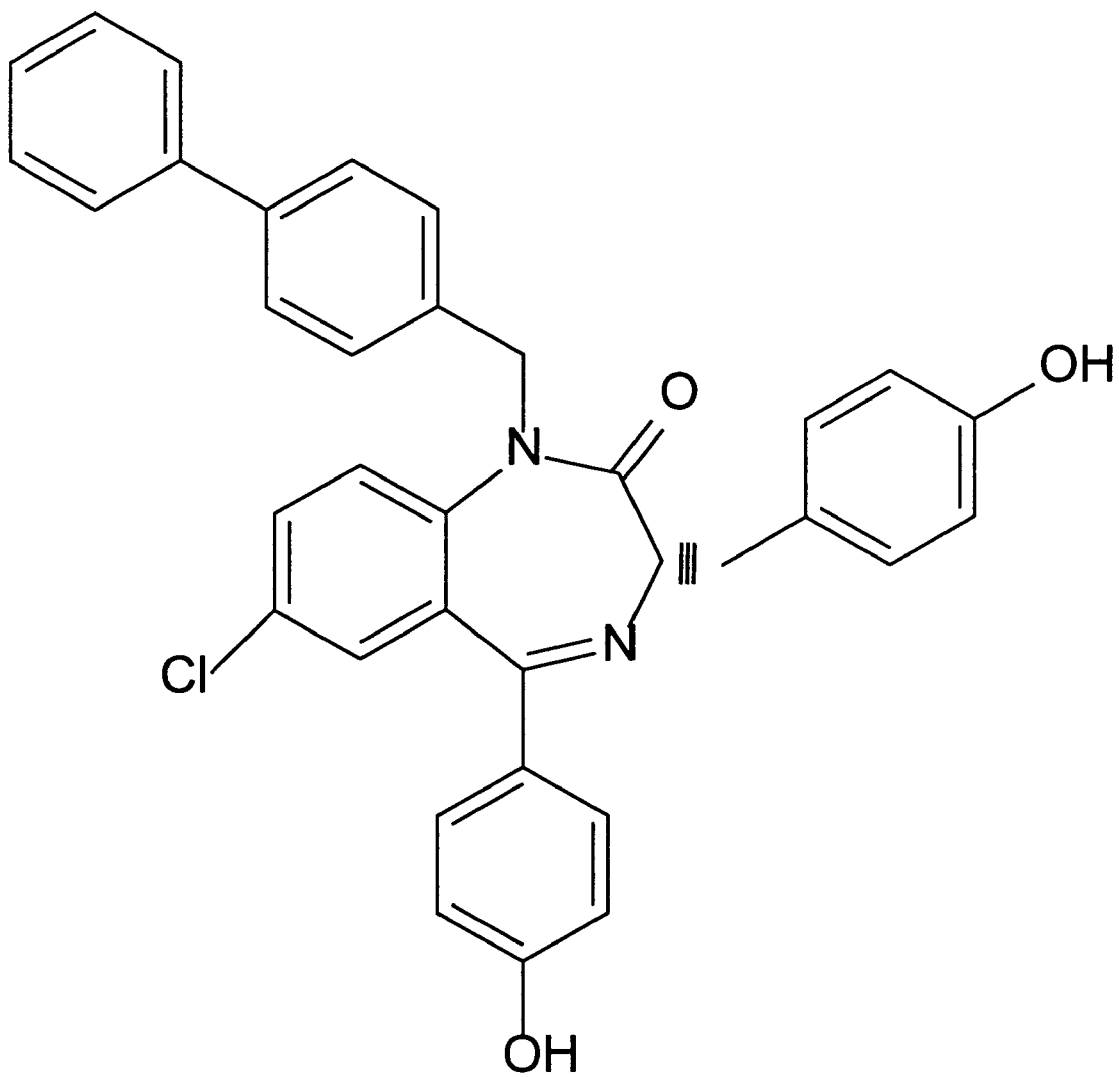
FIG. 5 shows the chemical structure of a preferred 1,4-benzodiazepine derivative.
Figure 6:
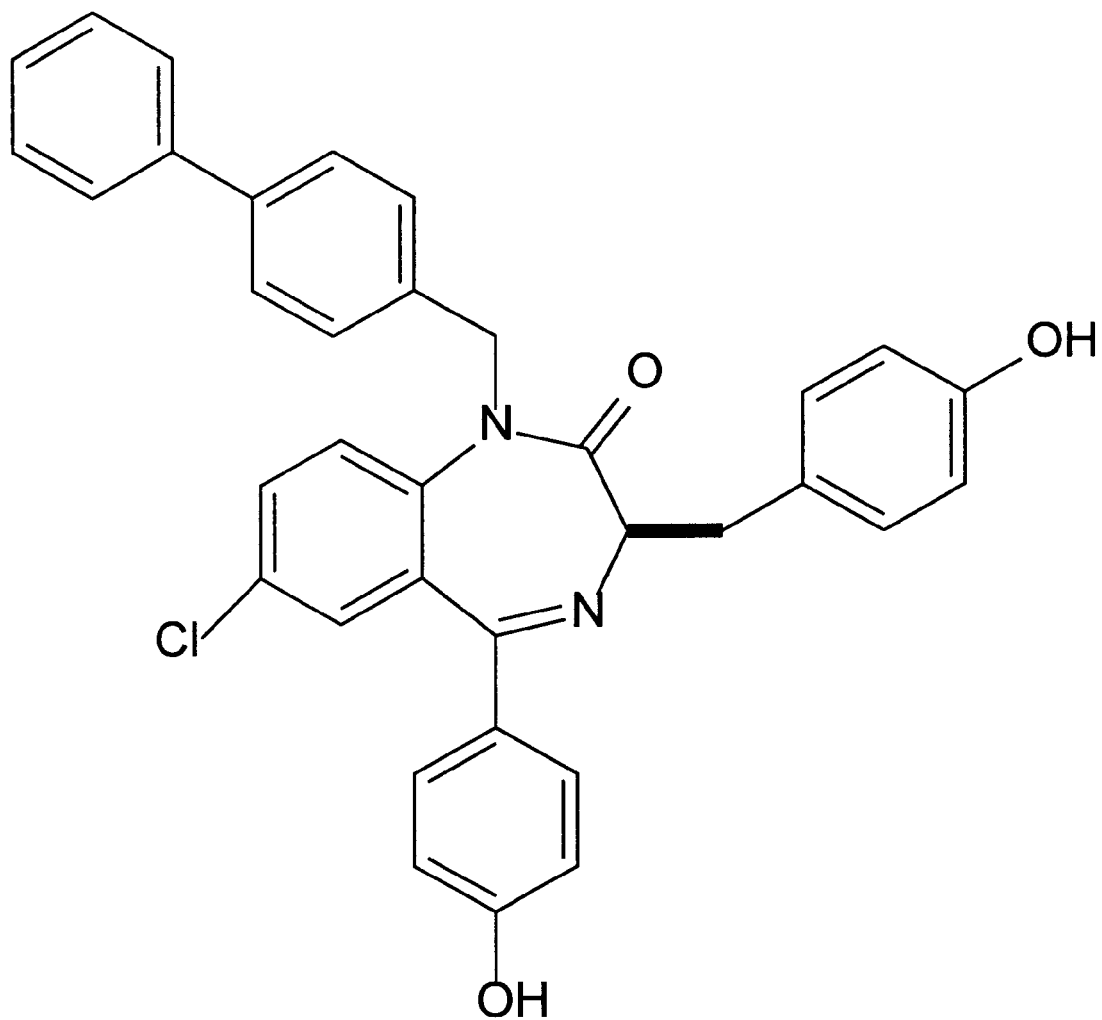
FIG. 6 shows the chemical structure of a preferred 1,4-benzodiazepine derivative.
Figure 7:
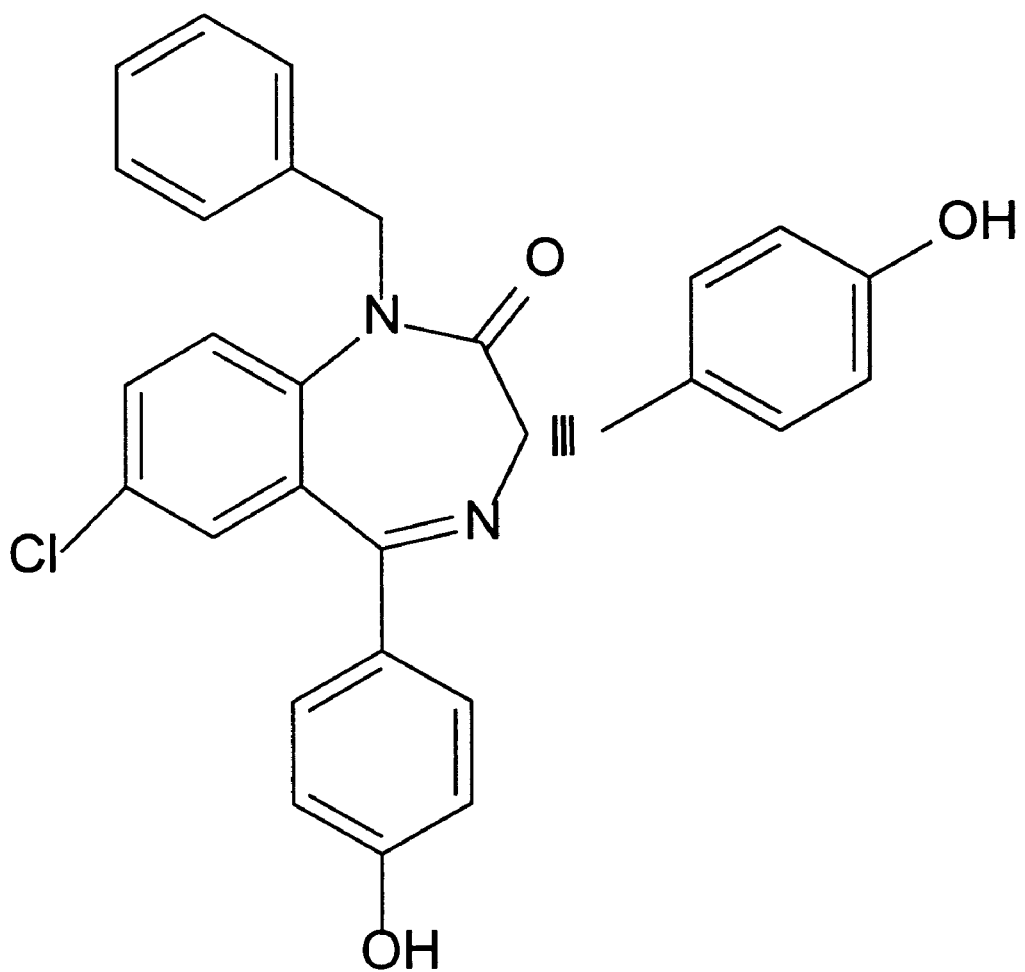
FIG. 7 shows the chemical structure of a preferred 1,4-benzodiazepine derivative.

$IC_{50}$ Values ($\mu$M) for 1,4-Benzodiazepine Inhibitors Identified in the Initial Library (see FIGS. 5, 6, and 7)

| Compound | Src | Csk | Abl | Lck | FGFr | PKA | HXK |
|---|---|---|---|---|---|---|---|
| L-Tyr,Bnz | 190 | 404 | 931 | 570 | 418 | 124 | 352 |
| L-Tyr,BnzPh | 73 | 136 | — | 505 | — | 450 | — |
| D-Tyr,BnzPh | 97 | 404 | — | 640 | 335 | 54 | — |

TABLE 12

Enzyme Specificity of L-Tyr,BnzPh

| Enzyme | $K_i$ ($\mu$M)* |
|---|---|
| Src | 20 |
| Csk | 63 |
| Yes | 50 |
| Abl | NI |
| Lck | NI |
| FGFr | NI |
| PKA | 104 |
| HXK | NI |
| LDH | NI |

*$K_i$ values are apparent values determined against variable poly $E_4Y$; NI = no inhibition or insufficient inhibition to determine a $K_i$ value.

EXAMPLE 6

Cellular Inhibition

A. Inhibition of the growth of HT-29 colon adenocarcinoma cells.

The HT-29 adenocarcinoma cell line is an established human cell line that possesses elevated Src activity. Non-specific PTK inhibitors such as herbimycin A have been shown to growth inhibit HT-29 and every colon tumor cell line with activated Src without affecting rare colon cell lines in which the enzyme is not activated (Garcia et al., 1991). Antisense to Src reduces the growth rate of these cells and greatly reduces their clonogenicity in soft-agar and tumorigenicity in nude mice (Staley et al., 1995). Therefore, the HT-29 cell line serves as a useful model for the study of Src inhibitors.

B. Growth of HT-29 and AF-B13 Cells.

For these assays $2 \times 10^4$ cells are plated in 24 well multiwell tissue culture dishes, in 1 ml of DME/F12 media supplemented with 5% fetal bovine serum. After 24 h, media is replaced with fresh media containing the concentration of inhibitor to be tested, or no inhibitor as a control. Cells are counted 1, 3, and 5 days subsequent to addition of inhibitor. For the day 5 counts, media with fresh inhibitor is used to replace spent media after day 3. The inventors have found that even with labile inhibitors such as coumarin derivatives, this regiment is sufficient to detect growth inhibition of effective inhibitors. For counting viable cells, cultures are trypsinized, stained with trypan blue, and cell number determined by counting under light microscopy with the use of a hemacytometer. Benzodiazepine derivatives were tested at their maximally soluble concentrations in 0.1% DMSO diluted with tissue culture medium, and serial dilutions were made thereof. Every concentration tested was performed in triplicate, in identical wells under identical assay conditions.

C. Anchorage-Independent Growth.

Soft agar colony formation is used to determine anchorage independent growth, an in vitro parameter which correlates well with tumorigenicity of HT 29 cells. (AFB-13 cells are unable to form soft agar colonies, a characteristic of normal cells). These assays are performed in 6 well (60 mm) multiwell tissue culture dishes. The wells are underlayed with 1% low melting agarose in complete growth media, and refrigerated for 15 min. $1 \times 10^3$ HT 29 cells are then added to the wells in complete media in 0.5% low melting agarose. The inventors have experimented with several different numbers of HT 29 cells and found that 1000 cells consistently yield between 200–300 colonies for "untreated" HT 29 cells. After a 24 h incubation period, 0.5 mL of media containing compound to be tested (or media alone as a control) is added to the dish. During the assay, media with or without the test compound is replenished every 3 days. Colonies estimated to contain >100 cells are counted after 14 days. For compounds that induce growth inhibition, the assay is continued to 28 days to assure that differences in colony forming ability were not due to altered growth rate of cells. For initial screening, assays are performed in duplicate for each compound to be tested, due to the large amount of inhibitor required for the length of the study.

Compound L-Tyr,BnzPh which had the highest in vitro selectivity (Tables 11 and 12) showed complete inhibition of colony formation of HT-29 colon adenocarcinoma cells at 28 $\mu$M concentration of the inhibitor. As a control for cellular toxicity, compounds were also tested for the growth inhibition of AFB-13, a normal human fibroblast cell line. Less than 10% inhibition of growth of AFB-13 normal fibroblasts was seen at the same concentrations. Compound L-Tyr,Bnz showed complete inhibition of colony formation of HT-29 colon adenocarcinoma cells at 30 $\mu$M concentrations of the inhibitor. Within experimental error, no inhibition of growth of AFB-13 normal fibroblasts was seen at the same concentrations. These results demonstrate the potential for these inhibitors to show specificity for inhibition of growth of human tumor cells in which the target enzyme, Src, is activated.

TABLE 13

Fffect of Select Benzodiazepines (see FIGS. 5, 6, and 7) on HT-29 Colon Adenocarcinoma Cells and AFB-13 Normal Human Fibroblasts*

| Concentration ($\mu$M) | HT-29 Growth[a] | HT-29 Colony Formation[b] | AFB-13 Growth[a] |
|---|---|---|---|
| L-Tyr,Bnz | | | |
| 0 | 100 ± 5 | 100 | 100 ± 6 |
| 3 | 100 ± 3 | 52 | 100 ± 4 |
| 15 | 84 ± 6 | 11 | 92 ± 6 |
| 30 | 73 ± 9 | 0 | 92 ± 8 |
| D-Tyr,BnzPh | | | |

TABLE 13-continued

Effect of Select Benzodiazepines (see FIGS. 5, 6, and 7) on HT-29
Colon Adenocarcinoma Cells and AFB-13 Normal Human Fibroblasts*

| Concentration ($\mu$M) | HT-29 Growth[a] | HT-29 Colony Formation[b] | AFB-13 Growth[a] |
|---|---|---|---|
| 0 | 100 ± 5 | 100 | 100 ± 6 |
| 3 | 94 ± 9 | 94 | 89 ± 6 |
| 16 | 74 ± 5 | 90 | 100 ± 4 |
| 32 | cytotoxic | 100 | 100 ± 7 |
| L-Tyr,BnzPh | | | |
| 0 | 100 ± 5 | 100 | 100 ± 6 |
| 3 | 100 ± 10 | 29 | 89 ± 6 |
| 14 | 98 ± 9 | 8 | 97 ± 5 |
| 28 | cytotoxic | 0 | 90 ± 4 |

*All values are expressed as a percent of control.
[a]Determined by viable cell count 5 days after plating.
[b]Determined for colonies ≧100 cells 14 days after plating.

EXAMPLE 7

Animal Studies

This example describes the methods, protocols, and screening criteria for animal studies involving protein tyrosine kinase inhibitors.

Specific drug inhibitors of protein tyrosine kinases are given to rodents by the intravenous and oral routes to establish their distribution and metabolism using standard pharmacokinetic methods. Assays for each drug are developed using commonly used analytical techniques of high-performance liquid chromatography (HPLC), and/or mass spectroscopy (MS).

Toxicity to these agents is determined in rodents via conventional dose-schedule methods to arrive at the maximum-tolerated dose of drug that can be given to rodents having tumors without significant damage to the animal.

In vivo testing of inhibitor drugs is carried out in immunosuppressed rodents that are growing tumors from human tumor cell lines. The drugs are administered by the intraperitoneal, oral, and/or intravenous routes. Dosing is dependent on the prior establishment of the pharmacokinetic distribution pattern of the drugs and the further establishment of a relatively non-toxic dose schedule in the host animal. End-points of drug efficacy (antitumor activity) are the failure of tumors to grow, the reduction in existing tumors, and/or increased life-span of rodents with tumors resulting from the use of protein tyrosine kinase drug inhibitors. The ability of these drugs to reduce tumor growth in different tumors and different locations in rodents are also evaluated. For some studies, absolute increases in life-span in control rodents not receiving drugs are compared to rodents with tumors who are receiving drugs.

EXAMPLE 8

Human Studies

This example describes the methods, protocols, and screening criteria for human studies involving protein tyrosine kinase inhibitors.

Drugs that are found safe for rodents with activity against rodents with human tumors are evaluated further for toxicity by testing for longer periods of times in normal rodents and dogs. This ensures that these drugs are relatively non-toxic to these animals before they are tested in humans. Following the demonstration of safety in these studies, a drug or drugs from this family is studied in humans to determine its pharmacokinetic distribution and metabolism. Depending on the toxicity profile obtained in animals, the drug(s) may undergo pharmacokinetic studies in normal human volunteers or humans with cancer that volunteer.

Following or concomitant with these studies, humans with cancer are studied using conventional methodology for Phase 1 study of drug safety. These studies allow for the establishment of a safe dose for subsequent Phase 2 studies of antitumor efficacy in humans. Recommended adult dosages for benzodiazepine drugs currently known in the art are typically in the range of 30 to 60 mg per day, administered intravenously or orally. It is contemplated for purposes of the present invention that dosages of protein tyrosine kinase inhibitor drugs ranging from as low as 1 mg per day to as high as 1000 mg per day, administered parenterally, topically, or orally, may prove both efficacious and necessary.

The studies of efficacy are typically carried out in patients in whom a tumor has recurred or progressed following more conventional treatment. Drug(s) that demonstrate good antitumor activity and safety during Phase 2 study are further studied in combination with other drugs and/or in Phase 3 studies to determine whether they surpass currently accepted therapies.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compostions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The folowing references, to the extent that they provide exemplary procedural or other details supplementary to those set forth herein, are specifically incorporated herein by reference.

Barnekow, "Functional Aspects of the c-src Gene," *Crit. Rev. Oncogenesis,* 1:277, 1989.

Bjelfman, Hedborg, Johansson, Nordenskjold, Pahlman, "Expression of the Neuronal Form of $pp60^{c\text{-}src}$ in Neuroblastoma in Relation to Clinical Stage and Prognosis," *Cancer Res.,* 50:6908, 1990.

Bock, Dipardo, Evans, Rittle, Whitter, Veber, Anderson, Freidinger, *J. Med. Chem.,* 32:13, 1989.

Bolen, Rosen, Israel, "Increased $pp60^{c\text{-}Src}$ Tyrosyl Kinase Activity in Human Neuroblastomas is Associated With Amino-Terminal Tyrosine Phosphorylation of the src Gene Product," *Proc. Natl. Acad. Sci.,* 82:7275, 1985.

Bolen, Veillette, Schwartz, Deseau, Rosen, "Activation of $pp60^{c\text{-}Src}$ Protein Kinase Activity in Human Colon Carcinoma," *Proc. Natl. Acad. Sci. USA,* 84:2251, 1987b.

Bolen, Veillette, Schwartz, Deseau, Rosen, "Analysis of $pp60^{c\text{-}src}$ in Human Colon Carcinoma and Normal Human Colon Mucosal Cells," *Oncogene Res.,* 1:149, 1987a.

Bondinell, Callahan, Huffman, Keenan, Ku, Newlander, Int. Pat. Appl. WO 93/00095, 1993.

Boojamra, Burow, Ellman, *J. Org. Chem.*, 60:5700, 1995.

Budde, Ke, Levin, "Activity of pp60$^{c-src}$ in 60 Different Cell Lines Derived from Human Tumors," *Cancer Biochem. Biophys.*, 14:171, 1994.

Budde, Obeyesekere, Ke, McMurray, "Use of Synthetic Peptides and Copolymers to Study Substrate Specificity and Inhibition of the Protein Tyrosine Kinase pp60$^{c-src}$," *Biochem. Biophys. Acta.*, 1248:50, 1995.

Budde, Rarndas, Ke, "Recombinant Src from Baculovirus-Infected Insect Cells: Purification and Characterization," *Preparative Biochem.*, 23:493, 1993.

Bunin and Ellman, *J. Am. Chem. Sci.*, 114:10997, 1992.

Bunin, Plunkett, Ellman, *Methods in Enzymology*, 267, 1996.

Bunin, Plunkett, Ellman, *Proc. Natl. Acad Sci. USA*, 91:4708, 1994.

Burke, "Protein-Tyrosine Kinase Inhibitors," *Drugs of the Future*, 17:119, 1992.

Burke, "Protein-Tyrosine Kinases: Potential Targets for Anticancer Drug Design," *Stem Cells*, 12:1, 1994.

Burke, Lim, Marquez, Li, Bolen, Stefanova, Horak, "Bicyclic Compounds as Ring Constrained Inhibitors of Protein-Tyrosine Kinase p56$^{lck}$," *J. Med. Chem.*, 36:425, 1993.

Carpino, Satat-Aalaee, Chao, DeSelms, *J. Am. Chem. Soc.*, 112:9651, 1990.

Cartwright, Kamps, Meisler, Pipas, Eckhart, "pp60$^{c-src}$ Activation in Human Colon Carcinoma," *J. Clin. Invest.*, 83:2025, 1989.

Cartwright, Meisler, Eckhart, "Activation of the pp60$^{c-src}$ Protein Kinase is an Early Event in Colonic Carcinogenesis," *Proc. Natl. Acad. Sci. USA*, 87:558, 1990.

Casnellie, Harrison, Pike, Helstrom, Krebs, "Phosphorylation of Synthetic Peptides by a Tyrosine Protein Kinase from the Particulate Fraction of a Lymphoma Cell Line," *Proc. Natl. Acad. Sci. USA*, 79:282, 1982.

Chackalaparampil and Shalloway, "Altered Phosphorylation and Activation of pp60$^{c-src}$ During Fibroblast Mitosis. *Cell*, 52:801, 1988.

Chang and Geahlen, "Protein-Tyrosine Kinase Inhibition: Mechanism-Based Discovery of Anti-Tumor Agents," *J. Nat. Prod.*, 55:1529, 1992.

Chen, Boiziau, Parker, Maillet, Commercon, Tocque, LePecq, Roques, Garbay, "Structure-Activity Relationships in a Series of 5-[(2,5-dihydroxybenzyl)amino] Salicylate Inhibitors of EGF-Receptor-Associated Tyrosine Kinase: Importance of Additional Hydrophobic Aromatic Interactions," *J. Med. Chem.*, 37:845, 1994.

Conradi, Hilgers, Ho, Burton, "The Influence of Peptide Structure on Transport Across Caco-2 Cells," *Pharm. Res.*, 8:1453, 1991.

Cushman, Chinnasamy, Chakkraborti, Jurayj, Geahlen, Haugwitz, "Synthesis of [(4-pyridyl-1-oxide)-L-Alanine$^4$]-Angiotensin I as a Potential Suicide Substrate for Protein-Tyrosine Kinases," *Int. J. Pept. Prot. Res.*, 36:538, 1990.

Cushman, Nagarathnam, Burg, Geahlen, "Synthesis and Protein-Tyrosine Kinase Inhibitory Activities of Flavonoid Analogues," *J. Med. Chem.*, 34:798, 1991c.

Cushman, Nagarathnam, Gopol, Geahlen, "Synthesis and Evaluation of New Protein-Tyrosine Kinase Inhibitors. Part 1. Pyridine-Containing Stilbenes and Amides," *Biorg. Med. Chem. Lett.*, 1:211, 1991a.

Cushman, Nagarathnam, Gopol, Geahlen, "Synthesis and Evaluation of New Protein-Tyrosine Kinase Inhibitors. Part 2. Phenylhydrazones," *Biorg. Med. Chem. Lett.*, 1:215, 1991b.

DeWitt Kiely, Stankovic, Schroeder, Cody, Pavia, *Proc. Natl. Acad. Sci. USA*, 90:6909, 1993.

Dow, Chou, Bechle, Goddard, C. and Larson, E. R. "Identification of Tricyclic Analogs Related to Ellagic Acid as Potent/Selective Tyrosine Protein Kinase Inhibitors," *J. Med. Chem.*, 37:2224, 1994.

Fanning, Bulovas, Saini, Libertino, Joyce, Summerhayes, "Elevated Expression of pp60$^{c-src}$ in Low Grade Human Bladder Carcinoma," *Cancer Res*, 52:1457, 1992.

Fields and Noble, *Int. J. Peptide Protein Res.*, 35:161, 1990.

Fodor, et al., *Science* 251:767, 1991.

Fry, Kraker, McMichael, Ambroso, Nelson, Leopold, Conners, Bridges, "A Specific Inhibitor of the Epidermal Growth Factor Receptor Tyrosine Kinase," *Science*, 265:1093, 1994.

Frye, Johnson, Valvano, *J. Org. Chem.*, 56:3750, 1991.

Furka, Sebestyen, Asgendom, Dibo, *Int. J. Peptide Protein Res.*, 37:487, 1991.

Gallop, Barrett, Dower, Fodor, Gordon, *J. Med. Chem.*, 37:1233, 1994.

Garcia, Saya, Gallick, "The Ansimycin Antibiotic Herbimycin A Inhibits Colon Tumor Cell Lines by Interaction With pp60$^{c-src}$," *Oncogene*, 6:1983, 1991.

Garcia, Schoelson, George, Hinds, Goldberg, Miller, "Phosphorylation of Synthetic Peptides Containing Tyr-Met-X-Met Motifs by Nonreceptor Tyrosine Kinases in vitro.," *J. Biol. Chem.*, 268:25146, 1993.

Geysen, Rodda, Mason, Tribbick, Schoofs, *J. Immun. Methods*, 102:259, 1987.

Gold, Polisky, Uhlenbeck, Yarus, *Annu. Rev. Biochem.*, 64:763, 1995.

Gordon, Barrett, Dower, Fodor, Gallop, *J. Med. Chem.*, 37:1385, 1994.

Hall, Schaeublin, Missbach, "Evidence that c-src is Involved in the Process of Osteoclastic Bone Resorption," *Biochem. Biophys. Res. Commun.*, 199:1237, 1994.

Honeggar, Dull, Szapary, Komoriya, Kris, Ullrich, Schlessinger, "Kinetic Parameters of the Protein Tyrosine Kinase Activity of EGF-Receptor Mutants with Individually Altered Autophosphorylation Sites," *EMBO J*, 7:3053, 1988.

James, Goldstein, Brown, Rawson, Somers, McDowell, Crowley, Lucas, Levinson, Marsters, *Science*, 260:1937, 1993.

Jessup and Gallick, "The Biology of Colorectal Carcinoma," *Curr. Problems in Cancer*, 16:263, 1993.

Kitanaka, Waki, Kamano, Tanaka, "Antisense src expression Inhibits Proliferation and Erythropoietin-Induced Erythroid Differentiation of K562 Human Leukemia Cells," *Biochem. Biophysic Res. Commun.*, 201:1534, 1994.

Kornecki, Ehrlich, Lenox, *Science*, 226:1454, 1984.

Lain, Wu, Lou, "Identification and Characterization of a Novel Synthetic Peptide Substrate Specific for src-Family Protein Tyrosine Kinases," *Int. J. Peptide Prot. Res.*, 45:587, 1995.

Litwin, Cheng, Wang, "Purification of a pp60$^{c-src}$ Related Tyrosine that Effectively Phosphorylates a Synthetic Peptide Derived from p34cdc2," *J. Biol. Chem.*, 266:2557, 1991.

Luttrell, Lee, Lansing, Crosby, Jung, Willard, Luther, Rodriguez, Berman, Gilmer, "Involvement of pp60$^{c-src}$ with Two Major Signaling Pathways in Human Breast Cancer," *Proc. Natl. Acad. Sci.*, 91:83, 1994.

Lynch, Brugge, Fromowitz, Glantz, Wang, Caruso, Viola, "Increased Expression of the src Proto-Oncogene in Hairy Cell Leukemia and a Subgroup of B-Cell Lymphomas," *Leukemia*, 7:1416, 1993.

Maeji, Valerio, Bray, Campbell, Geysen, *Reactive Polymers,* 22:203, 1994.

Maquire, Sheets, McVety, Spada, Zilberstein, "A New Series of PDGF Receptor Tyrosine Kinase Inhibitors: 3-Substituted Quinoline Derivatives," *J. Med. Chem.,* 37:2129, 1994.

Navarro, Ghany, Racker, "Inhibition of Tyrosine Protein Kinases by Halomethyl Ketones," *Biochemistry,* 21:6138, 1982.

Novomy-Smith and Gallick, "Growth Modulation of Human Colorectal Carcinoma Cell Lines by Tumor Necrosis Factor Alpha Correlates with Changes in $pp60^{c-Src}$, *J. Immunother,* 11:159, 1992.

O'Donnel and Polt, "A Mild and Efficient Route to Schiff Base Derivatives of Amino Acids," *J. Org. Chem.,* 47:2663, 1982.

O'Shaughnessy, Deseau, Amini, Rosen, Bolen, "Analysis of the c-src Gene Product Structure, Abundance, and Protein Kinase Activity in Human Neuroblastoma and Glioblastoma Cells," *Oncogene Res.,* 2:1, 1987.

Ottenhoff-Kalff, Rijksen, van Beurden, Hennipman, Michels, Staal, *Cancer Res.,* 52:4773, 1992.

Parranch, "Immunohistochemically Demonstrated $pp60^{c-src}$ in Human Breast Carcinoma," *Oncology Reports,* 1:603, 1994.

Plunkett and Ellman, *J. Am. Chem. Soc.,* 117:3306, 1995a.

Plunkett and Ellman, *J. Org. Chem.,* 60:6006, 1995b.

Preis, Saya, Nadasdi, Hochhaus, Levin, Sadee, "Neuronal Cell Differentiation of Human Neuroblastoma Cells by Retinoic Acid Plus Herbimycin-A," *Cancer Res.,* 48:6530, 1988.

Punt, Rijksen, Vlug, Dekker, Staal, "Tyrosine Protein Kinase Activity in Normal and Leukemic Human Blood Cells," *Brit. J. Hematology,* 73:51, 1989.

Ramdas, Obeyesekere, McMurray, Budde, "A Synthetic Peptidic Substrate of Minimal Size and Semi-Optimal Sequence for the Protein Tyrosine Kinase $pp60^{c-src}$. *Archiv. Blochem. Biophys,* 326:73, 1996.

Romer, Buscher, Hill, Maurer, Petcher, Zeugner, Benson, Finner, Milkowski, Thies, *Nature,* 298:759, 1982.

Rosen, Bolen, Schwartz, Cohen, Deseau, Israel, "Analysis of $pp60^{c-src}$ Activity in Human Tumor Cell Lines and Tissues," *J. Biol. Chem.,* 261:13754, 1986.

Sabe, Okada, Nakagawa, Hanafusa, "Activation of c-Src in Cells Bearing v-Crk and Its suppression by Csk," *Mol Cell Biol.,* 12:4706–4713, 1992.

Shoelson, White, Kahn, "Nonphosphorylatable Substrate Analogs Selectively Block Autophosphorylation and Activation of the Insulin Receptor, Epidermal Growth Factor, and $pp60^{v-src}$ Kinases," *J. Biol. Chem.,* 264:7831, 1989.

Songyang, Carraway, Eck, Harrison, Feldman, Mohammadi, Schlessinger, Hubbard, Smith, Eng, Lorenzo, Ponder, Mayer, Cantley, "Catalytic Specificity of Protein-Tyrosine Kinases is Critical for Selective Signalling," *Nature,* 373:536, 1995

Soriano, Montogomery, Geske, Bradley, "Targeted Disruption of the c-src Proto-Oncogene Leads to Osteopetrosis in Mice," *Cell,* 64:693, 1991.

Staley, Parikh, Saya, Gallick, "Inhibition of in vitro and in vivo HT-29 Colon Adenocarcinoma Cell Line Growth by a c-src Antisense Expression Vector," Oral presentation, AACR Annual Meeting, Toronto, Canada, 1995.

Sternbach, *J. Med. Chem.,* 22:1, 1979.

Sun and Budde, "A Modified pGEX Expression System that Eliminates Degradation Products and Thrombin from the Recombinant Protein," *Analytical Biochem.,* 231:458, 1995.

Takeshima, Hamaguchi, Watanbe, Aldyama, Kataoka, Ohnishi, Xiao, Nagai, Takaagi, "Aberrant Elevation of Tyrosine-Specific Phosphorylation in Human Gastric Cancer Cells," *Japan J. Cancer Res.,* 82:1428, 1991.

Talamonti, Curley, Gallick, "Development and Progression of Human Colon Cancer," *Cancer Bull.,* 44:321, 1992.

Talamonti, Roh, Curley, Gallick, "Increase in Activity and Level of $pp60^{c-src}$ in Progressive Stages of Human Colorcoral Cancer," *J. Clin. Invest.,* 91:53, 1993.

Talamonti, Roh, Curley, Gallick, "The c-src Oncogene Participates in the Development of Human Colorectal Liver Metastases," *Surg. Forum,* 42:422, 1991.

Termuhlen, Curley, Talamonti, Saboorian, Gallick, "Site-Specific Differences in $pp60^{c-src}$ Activity in Human Colorectal Metastases," *J. Surg. Res.,* 54:293, 1993.

Thompson and Ellman, *Chem. Rev.,* 1996.

Thompson, Fry, Kraker, Denny, "Tyrosine Kinase Inhibitors. 2. Synthesis of 2,2'-dithiobis(1H-indole 3-alkanamides) and Investigation of Their Inhibitory Activity Against Epidermal Growth Factor Receptor and $pp60^{c-src}$ Protein Tyrosine Kinases" *J. Med. Chern.,* 37:598, 1994.

Valerio, Bray, Maeji, *Int. J. Peptide Protein Res.,* 44:158, 1994.

Waki, Kitanka, Kamano, Tanaka, Kubota, Ohnishi, Takahara, Irino, "Antisense SRC Expression Inhibits U937 Human Leukemia Cell Proliferation in Conjunction with Reduction of c-MYB Expression," *Biochem. Biophys. Res. Commun.,* 201:1001, 1994.

Waksman, Kominos, Robertson, Pant, Baltimore, Birge, Cowbum, Hanafusa, Mayer, Overduin, Resh, Rios, Silverman, Kuriyan, "Crystal Structure of the Phosphotyrosine Recognition Domain SH2 of v-src Complexed with Tyrosine-Phosphorylated Peptides," *Nature,* 358:646, 1992.

Walker, *J. Chem. Soc., p.*1929, 1962.

Ward, Cook, Slater, Davies, Holdgate, Green, "Epidermal Growth Factor Receptor Tyrosine Kinase Investigation of Catalytic Mechanism, Structure-Based Searching and Discovery of a Potent Inhibitor," *Biochem. Pharm.,* 48:659, 1994.

Wong and Goldberg, "In vitro Phosphorylation of Angiotensin Analogs by Tyrosyl Protein Kinases," *J. Biol. Chem.,* 258:1022, 1983.

Wong and Goldberg, "Kinetics and Mechanism of Angiotensin Phosphorylation by the Transforming Gene Product of Rous Sarcoma Virus," *J. Biol. Chem.,* 259:3127, 1984.

Yoneda, Lowe, Lee, Gutierrez, Niewolna, Williams, Izbicka, Uehara, Mindy, "Herbimycin a, A $pp60^{C-src}$ Kinase Inhibitor, Inhibits Osteoclastic nine Resorption in vitro and Hypercalcemia in vivo," *J. Clin. Invest.,* 91:2791, 1993.

Yuan, Jakes, Elliott, Graves, "A Rationale for the Design of an Inhibitor of Tyrosyl Kinases,". *J. Biol. Chem.,* 265:16205, 1990.

Zheng, Wang, Pallen, "Cell Transformation and Activation of $pp60^{c-src}$ by Overexpression of a Protein Tyrosine Phosphatase, *Nature,"* 359:336, 1992.

Zuckerman, *J. Org. Chem.,* 60:5700, 1995.

What is claimed is:

1. A compound represented by structural formula I,

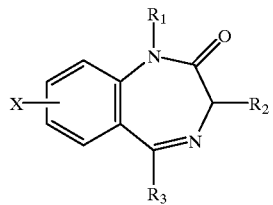

where $R_1$ is —$CH_2C_6H_5$, $R_2$ is p-hydroxy benzyl, $R_3$ is p-phenol, and X is 7-Cl, wherein said compound has the S configuration about the 3-carbon of the seven member ring, and salts of said compound.

2. A pharmaceutical composition comprising a pharmaceutically acceptable excipient and a compound represented by structural formula I,

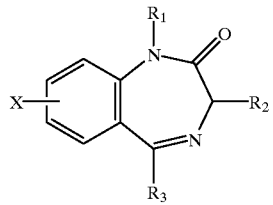

where $R_1$ is —$CH_2C_6H_5$, $R_2$ p-hydroxy benzyl, $R_3$ is p-phenol, and X is 7-Cl, wherein said compound has the S configuration about the 3-carbon of the seven member ring, and salts of said compound.

3. The composition of claim 2, wherein said composition is formulated for parenteral administration.

4. The composition of claim 2, wherein said composition is formulated for oral administration.

5. The composition of claim 2, wherein said composition is formulated for topical administration.

6. A method of inhibiting a protein tyrosine kinase comprising contacting a composition comprising a protein tyrosine kinase with an effective inhibitory amount of a compound represented by structural formula I,

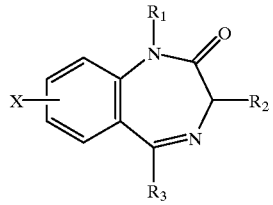

where $R_1$ is —$CH_2C_6H_5$, $R_2$ is p-hydroxy benzyl, $R_3$ is p-phenol, and X is 7-Cl, wherein said compound has the S configuration about the 3-carbon of the seven member ring, and salts of said compound.

7. The method of claim 6, wherein said protein tyrosine kinase is contained within a cell, and said compound is provided to said cell.

8. The method of claim 7, wherein said cell is located within a mammal and a pharmaceutically acceptable form of said compound is administered to said mammal.

9. The method of claim 8, wherein said mammal is a human subject.

10. The method of claim 6, wherein said composition comprises the protein tyrosine kinase $pp60^{Src}$.

11. The method of claim 6, wherein said composition comprises the protein tyrosine kinase FGFr.

12. A method of inhibiting a protein tyrosine kinase comprising administering to a mammal a biologically effective inhibitory amount of a pharmaceutical composition comprising a compound represented by structural formula I,

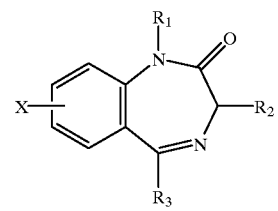

where $R_1$ is —$CH_2C_6H_5$, $R_2$ is p-hydroxy benzyl, $R_3$ is p-phenol, and X is 7-Cl, wherein said compound has the S configuration about the 3-carbon of the seven member ring and pharmaceutically acceptable salts of said compound.

13. The method of claim 12, wherein said composition inhibits abnormal cellular proliferation in said mammal.

14. The method of claim 12, wherein said composition inhibits a disease characterized by abnormal NMDA channel regulation in said mammal.

15. The method of claim 14, wherein said disease is Alzheimer's disease.

16. The method of claim 14, wherein said disease is Parkinson's disease.

17. The method of claim 14, wherein said disease is schizophrenia.

18. The method of claim 12, wherein said composition inhibits osteoporosis in said mammal.

19. The method of claim 12, wherein said composition inhibits artheroscierosis in said mammal.

20. The method of claim 12, wherein said composition inhibits angiogenesis in said mammal.

21. The method of claim 12, wherein said composition inhibits the proliferation of tumor cells in said mammal.

22. The method of claim 12, wherein said composition inhibits diabetic retinopathy in said mammal.

23. The method of claim 12, wherein said mammal is a human subject.

24. A method of treating cancer, comprising administering to a mammal with cancer a therapeutically effective inhibitory amount of a pharmaceutically acceptable composition comprising a compound represented by structural formula I,

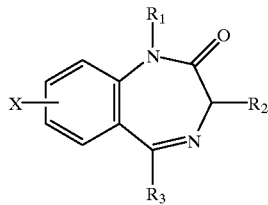

where $R_1$ is —$CH_2C_6H_5$, $R_2$ is p-hydroxy benzyl, $R_3$ is p-phenol, and X is 7-Cl, wherein said compound has the S configuration about the 3-carbon of the seven member ring, and pharmaceutically acceptable salts of said compound.

25. The method of claim 24, wherein said composition is injected into a tumor.

26. The method of claim 24, wherein said mammal is a human subject.

27. A method of treating a disease characterized by abnormal NMDA channel regulation, comprising administering to a mammal with abnormal NMDA channel regulation a therapeutically effective inhibitory amount of a pharmaceutically acceptable composition comprising a compound represented by structural formula I,

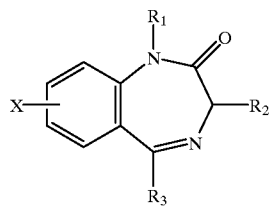

where $R_1$ is —$CH_2C_6H_5$, $R_2$ is p-hydroxy benzyl, $R_3$ is p-phenol, and X is 7-Cl, wherein said compound has the S configuration about the 3-carbon of the seven member ring, and pharmaceutically acceptable salts of said compound.

28. The method of claim 27, wherein said disease is Alzheimer's disease.

29. The method of claim 27, wherein said disease is Parkinson's disease.

30. The method of claim 27, wherein said disease is schizophrenia.

31. The method of claim 27, wherein said mammal is a human subject.

* * * * *

UNITED STATES PATENT AND TRADEMARK OFFICE
CERTIFICATE OF CORRECTION

PATENT NO.     :     6,100,254
DATED          :     August 8, 2000
INVENTOR(S)    :     Budda et al.

It is certified that error appears in the above-identified patent and that said Letters Patent is hereby corrected as shown below:

In claim 19, column 56, line 53, please delete "artheroscierosis" and insert -- artherosclerosis -- therefor.

Signed and Sealed this

Seventeenth Day of April, 2001

Attest:

NICHOLAS P. GODICI

Attesting Officer

Acting Director of the United States Patent and Trademark Office